United States Patent
Walsh

(10) Patent No.: US 7,368,420 B1
(45) Date of Patent: May 6, 2008

(54) AKT COMPOSITIONS FOR ENHANCING SURVIVAL OF CELLS

(75) Inventor: Kenneth Walsh, Carlisle, MA (US)

(73) Assignee: Caritas St. Elizabeth's Medical Center of Boston, Inc., Boston, MA (US)

(*) Notice: Subject to any disclaimer, the term of this patent is extended or adjusted under 35 U.S.C. 154(b) by 617 days.

(21) Appl. No.: 09/408,905

(22) Filed: Sep. 29, 1999

Related U.S. Application Data

(60) Provisional application No. 60/102,740, filed on Oct. 2, 1998.

(51) Int. Cl.
*A31K 31/713* (2006.01)

(52) U.S. Cl. ............................................ 514/2; 514/44
(58) Field of Classification Search .................... 514/2, 514/44; 424/184.1, 94.1
See application file for complete search history.

(56) References Cited

U.S. PATENT DOCUMENTS 5,681,703 A  10/1997  Tomei ........................... 435/6

FOREIGN PATENT DOCUMENTS

| WO | WO 92/11865 | 7/1992 |
| WO | WO 99/12559 | 3/1999 |

OTHER PUBLICATIONS

Cuevas et al. (Eur.J.Med.Res, vol. 2, pp. 465-468, Nov. 1997).*
Datta et al. (Cell, vol. 91, pp. 231-241, Oct. 1997).*
Crystal, R. (Science, vol. 270, 1995, pp. 404-410).*
Anderson, W. (Nature, 1998, vol. 392, pp. 25-30).*
Eck et al. (Goodman & Gilman's The Pharmacological Basis of Therapeutics (1996), 9th Edition, Chapter 5, McGraw-Hill, NY) (77-101).*
Verma et al. (1997) Nature vol. 389, p. 239-242, col. 3, paragraph 2.*
Marshall (1995) Science, vol. 269, p. 1054, col. 3, paragraph 2, and p. 1055, col. 1 (1050-1055).*
Rubanyi (Mol. Aspects Med. (2001) 22:113-142).*
Fujio, Y. and Walsh, K., "Akt Mediates Cytoprotection of Endothelial Cells by Vascular Endothelial Growth Factor in an Anchorage-dependent Manner", *J. Biol. Chem.*, 274:23:16349-16354 (1999).
Fujio, et al., "Cell Cycle Withdrawal Promotes Myogenic Induction of Akt, a Positive Modulator of Myocyte Survival", *Mol. Cell. Biol*, 19:7:5073-5082 (1999).
Eves, et al., "Akt, a target of phosphatidylinositol 3-kinase, inhibits apoptosis in a differentiating neuronal cell line", *Mol. Cell. Biol.* 18(4):2143-2152 (1998) (Abstract).
Crowder, R.J. and Freeman, R.S., "Phosphatidylinositol 3-kinase and Akt protein kinase are necessary and sufficient for the survival of nerve growth factor-dependent sympathetic neurons", *J. Neurosci.*, 15:18(8):2933-2943 (1998) (Abstract).
Hausler, et al., "Protection of CD95-mediated apoptosis by activation of phosphatidylinositide 3-kinase and protein kinase B", *Eur. J. Immunol.*, 28(1):57:-69 (1998) (Abstract).
Kennedy, et al., "The PI 3-kinase/Akt signaling pathway delivers an anti-apoptotic signal", *Genes Dev.*, 15:11(6):701-713 (1997) (Abstract).
Franke et al., "The Protein Kinase Encoded by the *Akt* Proto-Oncogene is a Target of the PDGF-Activated Phosphatidylinositol 3-Kinase," *Cell*, 81: 727-736, 1995.
Dudek H. et al., "Regulation of Neuronal Survival by the Serine-Threonine Protein Kinaase Akt," *Science*, Vo. 275, 1997, pp. 661-665.
Coffer et al., "Protein Kinase B (c-Akt): A Multifunctional Mediator of Phosphatidylinsitol 3-Kinase Activation," *Biochem J.*, 1998, vol. 335, pp. 1-13.
Mazure N. et al., "Induction of Vascular Endothelial Growth Factor by Hypoxia Is Modulated bya Phosphatidylinositol 3-Kinase/Akt Signaling Pathway in Ha-*ras*-Transformed Cells Through a Hypoxia Inducible Factor-1 Transcriptional Element," *Blood*, 1997, vol. 90, No. 9, pp. 3322-3331.
Burke P. et al., "Vascular Endothelial Growth Factor Causes Endothelial Proliferation After Vascular Injury," *Biochemical and Biophysical Research Communications*, 1995, vol. 207, No. 1, pp. 348-354.
Isner J.M. et al., "Gene Therapy for Arterial Disease," *The Lancet*, 1994, vol. 344, No. 8938, pp. 1653-1654.

\* cited by examiner

*Primary Examiner*—Brandon Fetterolf
(74) *Attorney, Agent, or Firm*—Wolf, Greenfield & Sacks, P.C.

(57) ABSTRACT

This invention relates to methods and compositions for the treatment of apoptotic cell-death. In particular the invention relates to Akt molecules and their use in inhibiting apoptotic cell-death in cardiomyocytes, skeletal myocytes and/or vascular endothelial cells. In view of these discoveries, Akt molecules can be used to inhibit apoptotic cell-death of any of the foregoing cells, and in particular, to treat conditions (e.g., myocardial infarction) that result in increased apoptotic cell-death of cardiomyocytes, skeletal myocytes and/or vascular endothelial cells.

4 Claims, 4 Drawing Sheets

AKT COMPOSITIONS FOR ENHANCING SURVIVAL OF CELLS

RELATED APPLICATIONS

This application claims priority under 35 USC §119(e) from U.S. Provisional Patent Application Ser. No. 60/102,740, filed on Oct. 2, 1998, now abandoned, entitled AKT COMPOSITIONS FOR ENHANCING SURVIVAL OF CELLS. The contents of the provisional application are hereby expressly incorporated by reference.

FEDERALLY SPONSORED RESEARCH

This invention was made with Government support under NIH Grants AG-15052, HL-50692 and AR-40197. The Government has certain rights to this invention.

FIELD OF THE INVENTION

This invention relates to methods and compositions for the treatment of apoptotic cell-death. In particular the invention relates to Akt molecules and their use in inhibiting apoptotic cell-death of cardiomyocytes, skeletal myocytes and/or vascular endothelial cells.

BACKGROUND OF THE INVENTION

Programmed cell-death (also known as apoptosis) is a form of cell-death defined by morphological and biochemical characteristics. Apoptosis is a characteristic of the normal developmental process as well as a response of cells to stress or other environmental insults. Apoptosis is characterized by membrane blebbing and retention of its integrity, cellular and cytoplasmic shrinkage, chromosome fragmentation and condensation, and endonuclease activation resulting in the characteristic 180 bp DNA ladder. During this process, the nuclear lamins are cleaved inducing their disassembly. Apoptosis does not induce an inflammatory response because cells form apoptotic bodies which are phagocytozed by neighboring cells. A number of stresses can induce apoptosis in vitro and in vivo. The administration of glucocorticoids, reduction of hormone and/or growth factor levels, chemotherapy (toxic agents), mechanical injury and DNA damage can all result in apoptosis. Apoptosis is also induced by aberrant cell cycle activity, and it can be triggered in cells that express the Fas receptor with crosslinking antibodies or the natural Fas ligand. High frequencies of apoptotic cell-death are associated in a diverse array of pathological disorders.

Akt (c-Akt) is a proto-oncogene encoding a serine-threonine kinase (Testa, J. R. and Bellacosa, A., *Leukemia Res.*, 1997, 21:1027-1031). It is the cellular homolog of the viral oncoprotein v-Akt, and is related to protein kinase-C (PKC) within the catalytic domain. However, c-Akt differs from the PKC family members by the presence of a pleckstrin homology (PH) domain at its N-terminus that is involved in the regulation of the activity of the enzyme by growth factors and intracellular signaling molecules. Various extracellular stimuli reportedly activate Akt through the phosphoinositide 3-kinase (PI 3-kinase) pathway (Datta, K. et al., *J. Biol. Chem.*, 1996, 271:30835-30839; Franke, T. F., et al., *Cell*, 1995, 81:727-736; King, W. G. et al., *Mol. Cell. Biol.*, 1997, 17:4406-4418). The lipid products of the PI 3-kinase reaction may activate Akt either by binding to the Akt pleckstrin homology domain (Franke, T. F. et al., 1997, *Cell*, 88:435:437), or by activating a protein kinase that phosphorylates Akt (Kohn, A. D., et al., *J. Biol. Chem.*, 1996, 271:21920-21926; Stokoe et al., *Science*, 1997, 277:567-570). Activation of Akt reportedly inhibits apoptosis induced by growth factor withdrawal or irradiation in neural cells, fibroblasts, and lymphocytes (Franke, T. F., et al., *Science*, 1997, 275:665-668; Hemmings, *Science*, 1997, 275:628-630). Recently, it has been reported that Akt phosphorylates the pro-apoptotic protein Bad leading to Bad inactivation and cell survival (Datta, K., et al., *Cell*, 1997, 91:231-241; Peso, L., et al., *Science*, 1997, 278:687-689).

SUMMARY OF THE INVENTION

The invention involves the discovery that Akt (also known as Protein Kinase-B, PKB) inhibits apoptotic cell-death of cells, and in particular, inhibits apoptotic cell-death of cardiomyocytes, skeletal myocytes and/or vascular endothelial cells. In view of these discoveries, it is believed that Akt molecules can be used to inhibit apoptotic cell-death of the afore-mentioned cell types, and in particular, to treat conditions (e.g., myocardial infarction) that result in increased apoptotic cell-death of cardiomyocytes, skeletal myocytes and/or vascular endothelial cells.

According to one aspect of the invention, a method for inhibiting apoptotic cell-death of cardiomyocytes in a subject in need of such treatment (e.g., a subject having a myocardial infarction) is provided. The method involves administering to a subject in need thereof an Akt molecule in an amount effective to inhibit apoptotic cell-death of cardiomyocytes in the subject. In the case of a subject having a myocardial infarction, administration of Akt molecules in an amount effective to inhibit apoptotic cell-death of cardiomyocytes in the subject, inhibits cardiac tissue necrosis. Subjects in need of such treatment may also include subjects with ischemia-reperfusion injury, dilated cardiomyopathy, and conductive system disorders.

Akt molecules according to the invention include wild-type Akt molecules and constitutively-active Akt molecules, described in more detail below. Preferably, when wild-type Akt molecules are used in the treatment of diseases associated with cardiomyocyte apoptotic cell-death (e.g., myocardial infarction, ischemia-reperfusion injury, dilated cardiomyopathy, conductive system disorders and the like), a growth factor may be co-administered. In preferred embodiments, Insulin-like Growth Factor-1 (IGF-1) is the growth factor preferably utilized. Most preferably, constitutively-active Akt molecules are utilized in the treatment of diseases associated with cardiomyocyte apoptotic cell-death, since their use negates the co-administration of a growth factor. In some embodiments, the Akt molecule is administered acutely to prevent future or further tissue damage (e.g., cardiac tissue necrosis). In preferred embodiments, acute administration of the Akt molecule is to the apical and anterolateral free wall of the heart.

In some embodiments, the cardiac tissue necrosis is mediated by increased apoptotic cell-death of cardiomyocytes. In other embodiments the cardiac tissue necrosis is mediated by increased apoptotic cell-death of cardiac tissue vascular endothelial cells. In important embodiments, the invention involves co-administration of at least one anti-atherosclerotic agent used in the treatment of an atherosclerotic condition, with at least one Akt molecule. In preferred embodiments, the anti-atherosclerotic agent is selected from the group consisting of a HMG-CoA reductase inhibitor, a diuretic, an antiadrenergic agent, a vasodilator, a calcium channel antagonist, an angiotensin-converting enzyme (ACE) inhibitor, an angiotensin II antagonist, and a clot dissolver together with an Akt molecule to treat myocardial infarction and inhibit cardiac tissue necrosis in the subject.

According to another aspect of the invention, a method for inhibiting apoptotic cell-death of cardiomyocytes is provided. The method involves contacting an Akt molecule with cardiomyocytes under conditions to permit entry of the Akt molecule into the cardiomyocytes, in an amount effective to inhibit apoptotic cell-death of the cardiomyocytes. In some embodiments, the contacting of an Akt molecule with a cardiomyocyte may comprise either acute or prophylactic administration of the Akt molecule. In important embodiments, the cardiomyocyte is part of a tissue or an organ to be transplanted. When the cardiomyocyte is part of a tissue or an organ to be transplanted, the contacting of an Akt molecule with the cardiomyocyte may also comprise either acute or prophylactic administration of the Akt molecule. As in the foregoing embodiments, when wild-type Akt molecules are used in inhibiting apoptotic cell-death of cardiomyocytes, a growth factor may be co-administered. In preferred embodiments, Insulin-like Growth Factor-1 (IGF-1) is the growth factor preferably utilized. Most preferably, constitutively-active Akt molecules are utilized.

According to yet another aspect of the invention, a method for inhibiting apoptotic cell-death of vascular endothelial cells is provided. The method involves contacting an Akt molecule with vascular endothelial cells under conditions to permit entry of the Akt molecule into the vascular endothelial cells, in an amount effective to inhibit apoptotic cell-death of the vascular endothelial cells. In important embodiments, the vascular endothelial cell is part of a tissue or an organ to be transplanted. When the vascular endothelial cell is part of a tissue or an organ to be transplanted, the contacting of an Akt molecule with the vascular endothelial cell may comprise either acute or prophylactic administration of the Akt molecule. Similar to the foregoing embodiments relating to a cardiomyocyte, when wild-type Akt molecules are used in inhibiting apoptotic cell-death of vascular endothelial cells, a growth factor may be co-administered. In preferred embodiments, Vascular Endothelial Growth Factor (VEGF) is the growth factor preferably utilized. Most preferably, constitutively-active Akt molecules are utilized.

In another aspect of the invention, a method for treating a condition associated with increased apoptotic cell-death of vascular endothelial cells is provided. The method involves administering to a subject in need of such treatment an Akt molecule in an amount effective to inhibit increased apoptotic cell-death of vascular endothelial cells. As described in the foregoing embodiments, when wild-type Akt molecules are used in inhibiting apoptotic cell-death of vascular endothelial cells, a growth factor is preferably co-administered. In preferred embodiments, Vascular Endothelial Growth Factor (VEGF) is the growth factor preferably utilized. Most preferably, constitutively-active Akt molecules are utilized. In certain embodiments, the condition is characterized by lesions of a blood vessel wall. In preferred embodiments, lesions of a blood vessel wall (also known as endothelial cell dysfunction) are associated with hyperlipidemic subjects. In other preferred embodiments, the Akt molecule is administered acutely to prevent future or further tissue damage (e.g., endothelial cell dysfunction).

In yet another aspect of the invention a method for inhibiting apoptotic cell-death of skeletal myocytes is provided. The method involves contacting an Akt molecule with skeletal myocytes under conditions to permit entry of the Akt molecule into the skeletal myocytes, in an amount effective to inhibit apoptotic cell-death of the skeletal myocytes. In one embodiment, the skeletal myocytes are differentiating skeletal myocytes. In important embodiments, the skeletal myocyte is part of a tissue or an organ to be transplanted.

According to another aspect of the invention, a method for treating a condition associated with increased apoptotic cell-death of skeletal myocytes, is provided. The method involves administering to a subject in need of such treatment an Akt molecule in an amount effective to inhibit increased apoptotic cell-death of skeletal myocytes. In one embodiment, the skeletal myocytes are differentiating skeletal myocytes. In another embodiment, the condition is selected from the group consisting of muscular dystrophy, spinal muscular atrophy, anabolic steroid-induced muscle injury, skeletal muscle oxidative stress, physical exercise, and unloading-induced skeletal muscle atrophy.

The invention also involves an isolated human Akt nucleic acid operably linked to a gene expression sequence, wherein the gene expression sequence permits expression of the Akt nucleic acid in a eukaryotic cell selected from the group consisting of a cardiomyocyte, a skeletal muscle cell and a vascular endothelial cell. Preferably the nucleic acid is contained in an appropriate expression vector (e.g., adenoviral vector, modified adenoviral vector, retroviral vector, plasmid, liposome) to more efficiently genetically modify the targeted cell and achieve expression of Akt in the targeted cell. In certain embodiments, the eukaryotic cell is a cardiomyocyte. In other embodiments, the eukaryotic cell is a vascular endothelial cell. In yet other embodiments, the eukaryotic cell is a skeletal myocyte. In preferred embodiments, the vector is an adenoviral vector. In further embodiments, the foregoing Akt containing compositions further include at least one anti-atherosclerotic agent selected from the group consisting of a HMG-CoA reductase inhibitor, a diuretic, an antiadrenergic agent, a vasodilator, a calcium channel antagonist, an angiotensin-converting enzyme (ACE) inhibitor, an angiotensin II antagonist, and a clot dissolver.

According to a further aspect of the invention, a pharmaceutical composition that includes any of the foregoing isolated human Akt molecules in a pharmaceutically effective amount to inhibit apoptotic cell-death in any of the cells according to the invention, and a pharmaceutically acceptable carrier, is also provided. Methods for preparing such pharmaceutical compositions are also provided. Preferred Akt molecules including vectors, as well as additional agents that can be included in the pharmaceutical compositions are as described above.

According to another aspect of the invention, a screening assay method for determining whether a putative therapeutic agent modulates apoptotic cell-death of cells is provided. The method involves inducing apoptotic cell-death in a test sample containing one or more types of cells, contacting a putative inhibitory agent with the cells of the test sample under conditions to permit entry of the agent into the cell, determining a test sample index cell number, and comparing the test sample index cell number with a control index cell number of a control sample. The control sample contains cells that have been contacted with an Akt molecule under conditions to permit entry of the Akt molecule into the cells, and their index cell number is used as a reference number. The index cell number of the test sample as compared with the equivalent index cell number of the control sample is indicative of the inhibitory activity of the test agent in inhibiting death of the cells.

In one embodiment, the foregoing screening assay occurs in vitro. In preferred embodiments, the cells are selected from the group consisting of cardiac muscle cells (cardiomyocytes), skeletal muscle cells (skeletal myocytes) and vascular endothelial cells.

In another embodiment, the foregoing screening assay occurs in vivo. In preferred embodiments, the cells are cells of a subject from a tissue selected from the group consisting of myocardium, skeletal musculature and vascular endothelium.

These and other aspects of the invention, as well as various advantages and utilities, will be more apparent with reference to the detailed description of the preferred embodiments.

BRIEF DESCRIPTION OF THE DRAWINGS

FIG. 3 Inset: HUVEC cultures were infected with Ad-β-gal (β gal) or Ad-Akt (Akt) and incubated for 24 hours. After 30 min. serum starvation, cells were treated with 1 ng/ml of VEGF for 15 min. The cell lysates were prepared and immunoprecipitated with anti-Akt antibodies. The kinase activities were measured as described in Materials and Methods. Cultures infected with Ad-Akt displayed 75 and 65% less cell-death than control cultures at 1 and 10 ng/ml, respectively, while no decrease in cell-death was detected in the cultures exposed to serum-free media in the absence of VEGF. As anticipated, adenoviral transfection of Akt also enhanced Akt kinase activity (FIG. 3B, inset). Akt immunoprecipitates prepared from Ad-Akt-infected HUVEC cultures exhibited greater kinase activity than control cultures when exposed to 1 ng/ml VEGF, the concentration of factor that produced the greatest difference in survival between test conditions. These data show that forced Akt expression can enhance the sensitivity of endothelial cells to VEGF survival signals.

DETAILED DESCRIPTION OF THE INVENTION

Figure 1A:
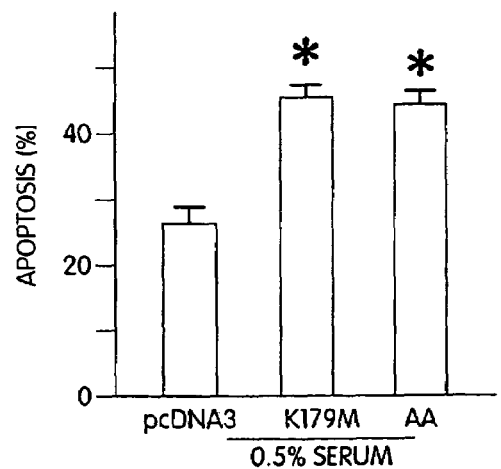
FIG. 1. Akt expression influences myocyte viability during differentiation. (A) Quantification of apoptosis induced by the dominant-negative Akt expression plasmids; (B) Wild-type Akt promotes myocyte survival.

The invention involves the discovery that Akt (also known as Protein Kinase-B, PKB) inhibits apoptotic cell-death of cells, and in particular, inhibits apoptotic cell-death of cardiomyocytes, skeletal myocytes and/or vascular endothelial cells. In view of these discoveries, it is believed that Akt molecules can be used to inhibit apoptotic cell-death of the foregoing cell types, and in particular, to treat conditions (e.g., myocardial infarction) that result in increased apoptotic cell-death of cardiomyocytes, skeletal myocytes and/or vascular endothelial cells.

Additionally, methods for using these molecules in vivo or in vitro for the purpose of inhibiting apoptotic cell-death and methods for treating conditions associated with such cell-death are also provided.

The human and mouse Akt genes have been isolated and sequenced (Jones P F, et al., *Proc Natl Acad Sci USA,* 1991, 88(10):4171-5; Coffer, P. J. and Woodgett, J. R., *Eur. J. Biochem.,* 1991, 201:475-481; Bellacosa, A., et al., Oncogene, 1993, 8:745-754). See also, Genbank Accession No. M63167 (SEQ. ID NOS. 1 and 2), Genbank Accession No. X61037 (SEQ ID NOS. 3 and 4) for the human Akt cDNA and predicted amino acid sequences, respectively, and Genbank Accession No. X65687 (SEQ ID NOS. 5 and 6) for the mouse Akt cDNA and predicted amino acid sequences, respectively. Although use of the mouse Akt compositions is exemplified in the Examples section, it is believed that the results obtained using such compositions are predictive of the results that may be obtained using the human sequences, since the mouse c-akt is 90% homologous to human Akt at the nucleic acid level and 98% homologous at the amino acid level. The c-akt protein contains, starting from its amino terminus, a src homology 2-like (SH2-like) domain (pleckstrin homology domain), and a kinase domain encoding a serine-threonine kinase with high degree of homology to members of the protein kinase C (PKC) family.

An "Akt molecule", as used herein, embraces both "Akt nucleic acids" and "Akt polypeptides" (discussed below). Akt molecules are capable of inhibiting apoptotic cell-death of a cell such as a cardiomyocyte, a skeletal myocyte or a vascular endothelial cell both in vivo and in vitro.

An "Akt nucleic acid", as used herein, refers to a nucleic acid molecule which: (1) hybridizes under stringent conditions to a nucleic acid having the sequence of SEQ ID NO. 1 and (2) codes for an Akt polypeptide (i.e., a polypeptide that inhibits apoptotic cell-death of cells, and in particular, inhibits apoptotic cell-death of cardiomyocytes, skeletal myocytes and vascular endothelial cells. Preferably the Akt polypeptide maintains a serine-threonine kinase activity. The preferred Akt nucleic acid has the nucleic acid sequence of SEQ ID NO. 1. The Akt nucleic acids of the invention also include homologs and alleles of a nucleic acid having the sequence of SEQ ID NO. 1, as well as functionally equivalent fragments, variants, and analogs of the foregoing nucleic acids. "Functionally equivalent", in reference to an Akt nucleic acid fragment, variant, or analog, refers to a nucleic acid that codes for an Akt polypeptide that inhibits apoptotic cell-death of cells, and in particular, inhibits apoptotic cell-death of cardiomyocytes, skeletal myocytes and vascular endothelial cells. Preferably the Akt polypeptide maintains a serine-threonine kinase activity. More specifically, "functionally equivalent" refers to an Akt polypeptide that has a serine-threonine kinase activity and is capable of enhancing survival of a cell that may undergo apoptotic cell-death.

The term "isolated", as used herein in reference to a nucleic acid molecule, means a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and gel separation. The term "isolated", as used herein in reference to a polypeptide (protein), means a polypeptide encoded by an isolated nucleic acid sequence, as well as polypeptides synthesized by, for example, chemical synthetic methods, and polypeptides separated from biological materials, and then purified using conventional protein analytical procedures.

In one embodiment, the Akt nucleic acid has the nucleotide sequence of SEQ. ID NO 1 ("Akt wild-type nucleic acid"), the nucleotide sequence encoding a "wild-type Akt polypeptide", i.e., the complete coding sequence of the gene encoding the human Akt.

In the preferred embodiments of the methods, the Akt nucleic acid is selected from the group consisting of a wild-type Akt nucleic acid (e.g., SEQ ID NO. 1, the coding region of SEQ ID NO. 1, SEQ ID NO. 3, and the coding region of SEQ ID NO. 3), and an Akt nucleic acid coupled with a myristoylation/palmitylation sequence, preferably the src myristoylation sequence (Franke, T. F., et al., *Cell*, 1995, 81:727-736). The myristoylation sequence serves as to help target and anchor the Akt polypeptide onto the cell membrane, thus rendering it constitutively active. The myristoylation sequence may also be placed in a number of different locations within SEQ ID NO. 1, as long as the serine threonine kinase activity of the encoded polypeptide remains intact (see later description of domains).

The Akt nucleic acid is operatively coupled to a promoter that can express Akt in a targeted cell (e.g., a cell selected from the group consisting of a cardiomyocyte, a skeletal myocyte and a vascular endothelial cell). Preferably, the nucleic acid is contained in an appropriate expression vector (e.g., adenoviral vector, modified adenoviral vector, retroviral vector, plasmid, liposome) to more efficiently genetically modify the targeted cell and achieve expression of multiple copies of the Akt polypeptide.

The Akt nucleic acid, in one embodiment, is operably linked to a gene expression sequence which directs the expression of the Akt nucleic acid within a eukaryotic cell selected from the group consisting of a cardiomyocyte, a skeletal myocyte and a vascular endothelial cell. The "gene expression sequence" is any regulatory nucleotide sequence, such as a promoter sequence or promoter-enhancer combination, which facilitates the efficient transcription and translation of the Akt nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, α-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined Akt nucleic acid. The gene expression sequences optionally includes enhancer sequences or upstream activator sequences as desired.

Preferably, the Akt nucleic acid of the invention is linked to a gene expression sequence which permits expression of the Akt nucleic acid in a cell selected from the group consisting of a cardiomyocyte, a skeletal myocyte and a vascular endothelial cell. More preferably, the gene expression sequence permits expression of the Akt nucleic acid in a cell selected from the group consisting of a cardiomyocyte, a skeletal myocyte and a vascular endothelial cell and does not permit expression of the Akt nucleic acid in a cell selected from the group consisting of a neuronal cell, a fibroblasts and a cell of hematopoietic origin. A sequence which permits expression of the Akt nucleic acid in a cell such as a cardiomyocyte, a skeletal myocyte and/or a vascular endothelial cell, is one which is selectively active in such a cell type, thereby causing expression of the Akt nucleic acid in these cells. The cardiac myosin heavy chain gene promoter, for example, can be used to express the Akt nucleic acid in a cardiomyocyte; the creatine kinase M gene promoter, for example, can be used to express the Akt nucleic acid in a skeletal myocyte; and the von Willebrand factor gene promoter, for example, can be used to express the Akt nucleic acid in a vascular endothelial cell. Those of ordinary skill in the art will be able to easily identify alternative promoters that are capable of expressing an Akt nucleic acid in any of the preferred cells of the invention.

The Akt nucleic acid sequence and the gene expression sequence are said to be "operably linked" when they are covalently linked in such a way as to place the transcription and/or translation of the Akt coding sequence under the influence or control of the gene expression sequence. If it is desired that the Akt sequence be translated into a functional protein, two DNA sequences are said to be operably linked if induction of a promoter in the 5' gene expression sequence results in the transcription of the Akt sequence and if the nature of the linkage between the two DNA sequences does not (1) result in the introduction of a frame-shift mutation, (2) interfere with the ability of the promoter region to direct the transcription of the Akt sequence, or (3) interfere with the ability of the corresponding RNA transcript to be translated into a protein. Thus, a gene expression sequence would be operably linked to an Akt nucleic acid sequence if the gene expression sequence were capable of effecting transcription of that Akt nucleic acid sequence such that the resulting transcript might be translated into the desired protein or polypeptide.

The Akt nucleic acids of the invention can be delivered to the preferred cell types of the invention alone or in association with a vector. In its broadest sense, a "vector" is any vehicle capable of facilitating: (1) delivery of an Akt molecule to a target cell and/or (2) uptake of an Akt molecule by a target cell. Preferably, the vectors transport the Akt molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing an Akt nucleic acid or an Akt protein) can be selectively delivered to a cardiomyocyte cell in, e.g., the myocardium. Methodologies for targeting include conjugates, such as those described in U.S. Pat. No. 5,391,723 to Priest. Another example of a well-known targeting vehicle is a liposome. Liposomes are commercially available from Gibco BRL. Numerous methods are published for making targeted liposomes. Preferably, the Akt molecules of the invention are targeted for delivery to cardiomyocytes, skeletal myocytes and vascular endothelial cells.

In general, the vectors useful in the invention include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hemopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

The preparation of an adeno virus containing a nucleic acid encoding the wild-type mouse Akt is described in the Examples. This construct is designated "Adeno-Akt" and contains a serotype 5 human replication defective adenovirus encoding the full-length murine Akt cDNA from the CMV promoter/enhancer). Human wild-type Adeno-Akt can be easily prepared by substituting the human wild-type or constitutively active Akt for the mouse Akt. For example, Adeno-Akt constructs can be constructed by subcloning the human Akt cDNA, (GenBank Accession No. M63167), downstream from an appropriate expression cassette (for example, the CMV promoter/enhancer) into the EcoRV site of the pCO1 vector containing the Ad5 adenoviral sequences required for homologous recombination. The resulting plasmid can then be linearized by restriction enzyme digestion and cotransfected in 293 cells with large ClaI fragment of the Ad5 d1324 viral DNA (Stratford-Perricaudet, L. D., et al., *J. Clin. Invest.*, 1993, 90:626-630). The resulting replication-defective recombinant adenoviral constructs are then purified from isolated plaques. The viral preparations are typically purified by two CsCl gradient centrifugations, dialyzed against buffer containing 10 mM Tris-Cl pH 7.5, 1 mM $MgCl_2$, and 135 mM NaCl and stored at $-80°$ C. in 10% glycerol. Viral titer is typically determined by plaque assay on 293 cells (Graham, F. L., and A. J. van der Eb, *Virology*, 1973, 52:456-463) and expressed as plaque forming units (pfu) per ml.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

Another preferred retroviral vector is the vector derived from the moloney murine leukemia virus, as described in Nabel, E. G., et al., *Science*, 1990, 249:1285-1288. These vectors reportedly were effective for the delivery of genes to all three layers of the arterial wall, including the media. Other preferred vectors are disclosed in Flugelman, et al., *Circulation*, 1992, 85:1110-1117. Additional vectors that are useful for delivering Akt are described in U.S. Pat. No. 5,674,722 by Mulligan, et. al.

In addition to the foregoing vectors, other delivery methods may be used to deliver an Akt molecule to a cell selected from the group consisting of a cardiomyocyte, a skeletal myocyte and a vascular endothelial cell, and facilitate uptake thereby. These additional delivery methods include, but are not limited to, natural or synthetic molecules, other than those derived from bacteriological or viral sources, capable of delivering the isolated Akt molecule to a cell.

A preferred such delivery method of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., *Trends Biochem. Sci.*, 1981, 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the myocardium or the vascular cell wall, by coupling the liposome to a specific ligand such as a monoclonal antibody, sugar, glycolipid, or protein. Ligands which may be useful for targeting a liposome to the vascular wall include, but are not limited to the viral coat protein of the Hemagglutinating virus of Japan. Additionally, the vector may be coupled to a nuclear targeting peptide, which will direct the Akt nucleic acid to the nucleus of the host cell.

Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985). Novel liposomes for the intracellular delivery of macromolecules, including nucleic acids, are also described in PCT International application no. PCT/US96/07572 (Publication No. WO 96/40060, entitled "Intracellular Delivery of Macromolecules").

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 08/213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the Akt nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein the Akt nucleic acid is dispersed throughout a solid polymeric matrix) or a microcapsule (wherein the Akt nucleic acid is stored in the core of a polymeric shell). Other forms of the polymeric matrix for containing the Akt nucleic acid include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver the Akt nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the Akt nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described Akt molecules for use as a medicament, methods for preparing the medicament and methods for the sustained release of the medicament in vivo.

Compaction agents also can be used in combination with a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the isolated Akt nucleic acid in a form that is more efficiently taken up by the cell or, more preferably, in combination with one or more of the above-described vectors.

Other exemplary compositions that can be used to facilitate uptake by a target cell of the Akt nucleic acids include calcium phosphate and other chemical mediators of intracellular transport, microinjection compositions, electroporation and homologous recombination compositions (e.g., for integrating an Akt nucleic acid into a preselected location within the target cell chromosome).

The Akt nucleic acids code for an Akt polypeptide. As used herein, an "Akt polypeptide" refers to a polypeptide that is coded for by an Akt nucleic acid and/or a structurally related molecule, and preferably has serine-threonine kinase activity. Akt polypeptides are useful for inhibiting apoptotic cell-death of a cell. The preferred Akt polypeptide of the invention has the amino acid sequence of SEQ ID NO. 2 (Akt "wild-type" polypeptide) or is a functionally equivalent fragment of SEQ ID NO.2 (e.g., the partial polypeptide of SEQ ID NO. 4, the polypeptide of SEQ ID NO. 6, etc.). Akt polypeptides further include functionally equivalent variants, and analogs of SEQ ID NO. 2, provided that the fragments, variants, and analogs preferably maintain serine-threonine kinase activity, and/or are capable of inhibiting apoptotic cell-death of a cell. The invention also embraces proteins and peptides coded for by any of the foregoing Akt nucleic acids.

By "structurally related," as used herein, refers to nucleic acids and polypeptides that are homologous and/or allelic to an Akt molecule. In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://wwww.ncbi.nlm.nih.gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

The preferred Akt nucleic acids of the invention encode the Akt having the amino acid sequence of SEQ ID NO. 2, the complete polypeptide sequence of the gene encoding the human Akt. This "wild type" human Akt polypeptide contains starting from its amino terminus, a pleckstrin homology domain (amino acids 5-108 of SEQ ID NO. 2), and a kinase domain encoding a serine-threonine kinase with high degree of homology to members of the protein kinase C (PKC) family (amino acids 150-408 of SEQ ID NO. 2).

Although use of the mouse Akt compositions is exemplified in the Examples section, it is believed that the results obtained using such compositions are predictive of the results that may be obtained using the human sequences, since the mouse c-akt is 98% homologous to human Akt at the amino acid level.

It will be appreciated by those skilled in the art that various modifications of the Akt polypeptide having the sequence of SEQ ID NO. 2 or functionally equivalent fragments of SEQ ID NO. 2 can be made without departing from the essential nature of the invention. Accordingly, it is intended that polypeptides which have the amino acid sequence of SEQ ID NO. 2 but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Fusion proteins, in which a peptide of the invention is coupled to a solid support (such as a polymeric bead), a carrier molecule (such as keyhole limpet hemocyanin), or a reporter group (such as radiolabel or other tag), or a membrane anchoring group (such a myristoylation peptide) also are embraced within the invention.

Preferred Akt polypeptides further include myristoylated Akt polypeptides. A myristoylation/palmitylation peptide sequence, preferably the src myristoylation peptide sequence, is coupled with the wild type Akt polypeptide (Franke, T. F., et al., *Cell,* 1995, 81:727-736). The myristoylation sequence serves as to help target and anchor the Akt polypeptide onto the cell membrane, thus rendering it constitutively active. Additionally, the myristoylation sequence may be coupled to an Akt polypeptide, with or without a linker, at any location within the polypeptide as long as the Akt polypeptide maintains its serine/threonine kinase activity. Moreover, the presence of a PH domain is not necessary for activity. For example, a fusion polypeptide containing the myristoylation sequence and the Akt serine/threonine kinase domain only and in the absence of all, or a part of, a PH domain, can still function and inhibit apoptotic cell-death of the preferred cells of the invention.

In one aspect, the invention involves a method for treating myocardial infarction in a subject. "Myocardial infarction" is a focus of necrosis resulting from inadequate perfusion of the cardiac tissue. Myocardial infarction generally occurs with the abrupt decrease in coronary blood flow that follows a thrombotic occlusion of a coronary artery previously narrowed by atherosclerosis. Generally, infarction occurs when an atherosclerotic plaque fissures, ruptures, or ulcerates, and a mural thrombus forms leading to coronary artery occlusion.

The diagnosis of myocardial infarction in a subject determines the need for treating the subject according to the methods of the invention. A number of laboratory tests, well known in the art, are described, for example, in Harrison's: Principles of Internal Medicine (McGraw Hill, Inc., New York). Generally, the tests may be divided into four main categories: (1) nonspecific indexes of tissue necrosis and inflammation, (2) electrocardiograms, (3) serum enzyme changes (e.g., creatine phosphokinase levels), and (4) cardiac imaging. A person of ordinary skill in the art could easily apply any of the foregoing tests to determine when a subject is at risk, is suffering, or has suffered, a myocardial infarction. A positively identified subject would thus benefit from a method of treatment of the invention.

According to the invention, the method involves administering to a subject having a myocardial infarction an Akt molecule in an amount effective to inhibit cardiac tissue necrosis in the subject. By "having a myocardial infarction" it is meant that the subject is at risk of developing, is currently having, or has suffered a myocardial infarction. It is believed that immediate administration of an Akt molecule would greatly benefit the subject by inhibiting apoptotic cell-death of cardiomyocytes (the cells mostly affected by the infarct) prior to, or following the infarct. By "immediate" it is meant that administration occurs before (if it is diagnosed in time), or within 48 hours from the myocardial infarct, although administration up to 14 days after the episode may also be beneficial to the subject.

In one embodiment, when wild-type Akt molecules are used in the treatment of diseases associated with cardiomyocyte apoptotic cell-death (e.g., myocardial infarction, ischemia-reperfusion injury, dilated cardiomyopathy, conductive system disorders and the like), a growth factor is preferably co-administered. In preferred embodiments, Insulin-like Growth Factor-1 (IGF-1) is the growth factor of choice. Most preferably, constitutively-active Akt molecules are utilized in the treatment of diseases associated with cardiomyocyte apoptotic cell-death, since their use negates the co-administration of a growth factor. In other words, no growth factor co-administration is necessary when the constitutively active form of Akt (e.g., the myristoylated form) is utilized.

The co-administered growth factor can act cooperatively, additively or synergistically with a wild-type Akt molecule of the invention to inhibit apoptotic cell-death of cardiomyocytes, conferring to their enhanced survival. The growth factor is administered in effective amounts. Such amounts maybe less than these sufficient to provide a therapeutic benefit when the growth factor is administered alone and not in combination with an Akt molecule. A person of ordinary skill in the art would be able to determine the effective amounts needed (see description below).

Preferred methods of administration for the Akt molecules of the invention in the treatment of the foregoing diseases associated with cardiomyocyte apoptotic cell-death include direct intramuscular injection into the myocardium, catheterization of the heart, and intraarterial administration. Intraarterial administration may be accompanied with a permeabilizing agent (e.g., nitric oxide), allowing easier access of the Akt molecules of the invention into the myocardium via the circulation.

In another aspect, the invention is directed to a method for treating a subject diagnosed as having a condition associated with increased apoptotic cell-death of a skeletal myocyte (skeletal muscle cell). Exemplary conditions that are caused by increased apoptotic cell-death of a skeletal myocyte are known to those of ordinary skill in the art and include, but are not limited to, the following diseases: muscular dystrophy (e.g., Duchenne), spinal muscular atrophy, anabolic steroid-induced muscle injury, skeletal muscle oxidative stress, physical exercise, and unloading-induced skeletal muscle atrophy. Preferred methods of administration include direct intramuscular injection. Examples of such modes of administration are described in Acsadi G, et al., *Nature*, 1991, 352(6338):815-818; Ragot T, et al., *Nature*, 1993, 361(6413):647-650; and Dunckley M G, et al., *Hum Mol Genet*, 1993, 2(6):717-723.

The Akt molecules of the invention are particularly useful for inhibiting apoptotic cell-death of vascular endothelial cells. The method involves administering to the subject an isolated Akt molecule in an amount and in a manner effective to inhibit apoptotic cell-death of a vascular endothelial cell. Exemplary conditions that are caused by increased apoptotic cell-death of a vascular endothelial cell are known to those of ordinary skill in the art and include, but are not limited to, vessel wall disease, and vascular endothelial cell dysfunction associated with hyperlipidemic subjects.

A "hyperlipidemic" subject is both a hypercholesterolemic and a hypertriglyceridemic subject. The current criteria established for human subjects are well known in the art (See, e.g., Harrison's Principles of Experimental Medicine, 13th Edition, McGraw-Hill, Inc., N.Y.). Hypercholesterolemic subjects and hypertriglyceridemic subjects are associated with increased incidence of premature coronary heart disease including vascular endothelial cell dysfunction. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a hyperlipidemic subject is defined as one whose cholesterol and triglyceride levels equal or exceed the limits set as described above for both the hypercholesterolemic and hypertriglyceridemic subjects.

Preferred methods of administration for the Akt molecules of the invention into subjects with apoptotic cell-death of vascular endothelial cells include intraarterial administration with clamping or locally via a balloon catheter (see later discussion). For example, in the case of intraarterial administration with clamping, the vessel wall in need of such treatment is "isolated" by clamping of the vessel on either side of the "injury" site, resulting in the temporary occlusion of the region to be treated, and allowing local delivery of the Akt molecules (e.g., by injection). In the case of intraarterial administration via a balloon catheter, the catheter is of the "soft-hydrogel surface" type.

The term "to permit entry" of an Akt molecule into a cell according to the invention has the following meanings depending upon the nature of the Akt molecule. For an Akt nucleic acid it is meant to describe entry of the nucleic acid through the cell membrane and into the cell nucleus, where upon the "Akt transgene" can utilize the cell machinery to produce functional Akt polypeptides. By "Akt transgene" it is meant to describe all of the Akt nucleic acids of the invention, including the "wild-type Akt" and the constitutively active Akt nucleic acids with or without the associated vectors. For an Akt polypeptide, it is meant to describe entry of the polypeptide through the cell membrane and into the cell cytoplasm, and utilization of the cell cytoplasmic machinery to produce a functional Akt polypeptide (one that inhibits apoptotic cell death of cells, and in particular, inhibits apoptotic cell-death of cardiomyocytes, skeletal myocytes and vascular endothelial cells. Preferably the Akt polypeptide maintains a serine-threonine kinase activity. In the case of the myristoylated Akt polypeptide, upon cytoplasmic enry, the molecule is expected to anchor onto the cell membrane.

The Akt molecules of the invention are administered in effective amounts. An effective amount is a dosage of the Akt nucleic acid sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with cardiomyocyte apoptotic cell-death during myocardial infarction, an effective amount is that amount which slows or inhibits the cardiomyocyte apoptotic cell-death associated with myocardial infarction. Likewise, an effective amount for treating skeletal myocyte apoptotic cell-death would be an amount sufficient to lessen or inhibit altogether skeletal myocyte apoptotic cell-death so as to slow or halt the development of or the progression of muscle degeneration. Thus, it will be understood that the Akt molecules of the invention can be used to treat the above-noted conditions prophylactically in subjects at risk of developing the foregoing conditions. By "acutely" it is meant that the Akt molecules of the invention are administered immediately and according to the preferred modes of administration of the particular disorder being treated. For example, in connection with cardiomyocyte apoptotic cell-death during myocardial infarction, the Akt molecules will be administered to a subject in need of such treatment preferably by intra-coronary (and including cross-clamping of the aorta) or intra-myocardial injection (see e.g., Hajjar R J, et al., *Proc Natl Acad Sci USA*, 1998, 95:5251-6). As used in the claims, "inhibit" embraces preventing and/or reducing in all of the foregoing. It is preferred generally that a maximum dose be used, that is, the highest safe dose according to sound medical judgment.

A subject, as used herein, refers to any mammal (preferably a human, and including a non-human primate, cow, horse, pig, sheep, goat, dog, cat or rodent) that may be susceptible to a condition associated with apoptotic cell-death of a cell (such as the conditions described above). Preferably the mammal is otherwise free of symptoms calling for Akt treatment. Reported conditions that have symptoms calling for treatment with an Akt molecule may also include conditions associated with apoptotic cell-death of neurons, lymphocytes and fibroblasts. Certain is subjects with a condition associated with an anomaly of calmodulin response (PCT/EP95/05052) are not in need of treatment according to the present invention and are therefore hereby expressly excluded.

The invention also contemplates methods for inhibiting apoptotic cell-death in a number of cell types that include, but are not limited to, cardiomyocytes, vascular endothelial cells, and/or skeletal myocytes. The method involves contacting an Akt molecule with a cell type of choice under conditions to permit entry of the Akt molecule into the cell type of choice, in an amount effective to inhibit apoptotic cell-death of the cell type of choice. In certain embodiments, the contacting of an Akt molecule with a cell type of choice according to the invention can comprise either acute or prophylactic administration of the Akt molecule. Such acute and/or prophylactic administration of the Akt molecule is particularly contemplated when the cell type of choice according to the invention contacted with the Akt molecule, is part of a tissue or an organ scheduled to be transplanted or implanted. Administration of the Akt molecule allows for longer term survival of the cells of the transplanted (implanted) tissue and/or organ under the adverse conditions the tissue and/or organ is subjected to during such procedure, i.e., ischemia, lower temperature, reperfusion, etc, therefore improving the tissue/organ's viability and/or acceptance by the recipient organism.

When used therapeutically, the isolated Akt molecules of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg//kg to about 20 mg/kg, in one or more dose administrations daily, for one or more days.

The therapeutically effective amount of the isolated Akt molecule is that amount effective to inhibit increased apoptotic cell-death of a cell, and in particular a cardiomyocyte, a skeletal myocyte and a vascular endothelial cell, and can be determined using, for example, standard tests known in the art. For example, TUNEL staining, and the appearance of condensed chromatin and other morphological features characteristic of apoptosis in electron micrographs can be used to assess apoptosis in the cells of the invention and other cell types.

Optionally, in the preferred embodiment of the invention for treating myocardial infarction, an isolated Akt molecule of the invention is administered to a subject in need of such treatment in combination with a method for treating an arteriosclerotic condition. An arteriosclerotic condition, as used herein, is a term of art that refers to classical atherosclerosis, accelerated atherosclerosis, atherosclerotic lesions and other physiological conditions characterized by undesirable vascular smooth muscle cell proliferation. See, e.g., Harrisons, Principles of Internal Medicine (McGraw Hill, Inc., New York) for a more detailed description of these conditions. The method for treating an arteriosclerotic condition may be a surgical method, an agent for treating restenosis, a method involving a drug therapy (e.g., gene therapy) or a combination of the foregoing.

Surgical methods for treating an arteriosclerotic condition include procedures such as bypass surgery, atherectomy, laser procedures, ultrasonic procedures, and balloon angioplasty. In a preferred embodiment of the invention, the isolated Akt molecule is administered to a subject in combination with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the vascular wall. As a result, the balloon surface is in contact layer of vascular endothelial cells on the surface of the vessel. The isolated Akt molecule is attached to the balloon angioplasty catheter in a manner which permits release of the isolated Akt molecule at the site of the atherosclerotic plaque. The isolated Akt molecule may be attached to the balloon angioplasty catheter in accordance with standard procedures known in the art. For example, the isolated Akt molecule may be stored in a compartment of the balloon angioplasty catheter until the balloon is inflated, at which point it is released into the local environment. Alternatively, the isolated Akt molecule may be impregnated on the balloon surface, such that it contacts the cells of the arterial wall as the balloon is inflated. The Akt molecule also may be delivered in a perforated balloon catheter such as those disclosed in Flugelman, et al., *Circulation*, v. 85, p. 1110-1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid or polypeptide to the balloon angioplasty catheter.

Additionally, the Akt molecule may be co-administered with an anti-atherosclerotic agent for treating or preventing clinically significant atherosclerosis. The term "co-administered," means administered substantially simultaneously with another agent. By substantially simultaneously, it is meant that an Akt molecule of the invention is administered to the subject close enough in time with the administration of the other agent (e.g., an anti-atherosclerotic agent, growth factor, etc.).

Preferred anti-atherosclerotic agents used in combination with the Akt molecule of the invention, include but are not limited to, the following drugs: HMG-CoA reductase inhibitors, diuretics, antiadrenergic agents, vasodilators, calcium channel antagonists, angiotensin-converting enzyme (ACE) inhibitors, angiotensin II antagonists, and clot dissolvers.

"HMG-CoA reductase (3-hydroxy-3-methylglutaryl-coenzyme A)" is the microsomal enzyme that catalyzes the rate limiting reaction in cholesterol biosynthesis (HMG-CoA6Mevalonate). An "HMG-CoA reductase inhibitor" inhibits HMG-CoA reductase, and therefore inhibits the synthesis of cholesterol. There is a large number of compounds described in the art that have been obtained naturally or synthetically, which have been seen to inhibit HMG-CoA reductase, and which form the category of agents useful for practicing the present invention. Traditionally these agents have been used to treat individuals with hypercholesterolemia. Examples include some which are commercially available, such as simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

Diuretics include thiazides, e.g., hydrochlorothiazide; loop acting diuretics, e.g., furosemide; potassium-sparing, e.g., spironolactone, triamterene, and amiloride.

Antiadrenergic agents include clonidine; guanabenz; guanfacine; methyldopa; trimethapajn; Rauwolfia alkaloids, e.g., reserpine; guanethidine; guanadrel; phentolamine; phenoxybenzamine; prazosin; terazosin; propranolol; metoprolol; nadolol; atenolol; timolol; timdolol; acebutolol; and labetalol.

Vasodilators include hydralazine; minoxidil; diazoxide; and nitroprusside.

Calcium channel antagonists include nisadipine; diltiazen; and verapamil.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(−1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche A G); A$_2$ agonists (Marion Merrill Dow) and certain non-peptide heterocycles (G.D.Searle and Company).

ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE, thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Drugs which are clot dissolvers include thrombolytic agents which have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v. 25 (7 suppl), p. 10S-17S(1995)). Thrombolytic agents include, for example, direct acting agents such as streptokinase and urokinase, and second generation agents such as tissue plasminogen activator (tPA).

Drugs which help contribute to the reduction of the plaque include cytostatic molecules and antisense agents to cell cycle regulatory molecules.

Certain cytokines function to strengthen the vascular wall by promoting endothelial cell proliferation. Cytokines which promote endothelial cell proliferation include, but are not limited, to the following: vascular endothelial growth factor (VEGF), basic fibroblast growth factor (bFGF), and acidic fibroblast growth factor (aFGF). Substances that stimulate the proliferation or migration of normal endothelial cells include factors which are associated with the vascularization of tumors and substances which inhibit angiogenesis. Such substances include transforming growth factor beta (TGFβ), tumor necrosis factor alpha (TNFα), human platelet factor 4 (PF4), and alpha interferon (αINF); factors which suppress cell migration, such as proteinase inhibitors, tissue inhibitors of metalloproteinase (TIMP-1 and TIMP-2); and other proteins such as protamine which has demonstrated angiostatic properties.

The above-described drug therapies are well known to those of ordinary skill in the art and are administered by modes known to those of skill in the art. The drug therapies are administered in amounts which are effective to achieve the physiological goals in combination with the isolated Akt molecules of the invention.

An isolated Akt molecule may be administered alone or in combination with the above-described drug therapies as part of a pharmaceutical composition. Such a pharmaceutical composition may include the isolated Akt molecule in combination with any standard physiologically and/or pharmaceutically acceptable carriers which are known in the art. The compositions should be sterile and contain a therapeutically effective amount of the isolated Akt molecule in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the Akt molecules, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Intramyocardial administration is preferred in patients suffering form myocardial infarction. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the Akt molecules into association with a carrier which constitutes one or more accessory ingredients. In general, the compositions are prepared by uniformly and intimately bringing the Akt molecules into association with a liquid carrier, a finely divided solid carrier, or both, and then, if necessary, shaping the product.

Compositions suitable for oral administration may be presented as discrete units, such as capsules, tablets, lozenges, each containing a predetermined amount of the Akt molecule. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the Akt molecules described above, increasing convenience to the subject and the physician. Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the Akt molecule is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The isolated Akt molecule may be administered alone or in combination with the above-described drug therapies by any conventional route, including injection or by gradual infusion over time. The administration may, for example, be oral, intravenous, intraperitoneal, intramuscular, intra-cavity, subcutaneous, or transdermal. When using the isolated Akt molecules of the invention, direct administration to the site with the increased apoptotic cell-death of a cell (e.g., a cardiomyocyte, a skeletal myocyte and a vascular endothelial cell) such as administration by injection, is preferred (see also earlier description).

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In general, the Akt nucleic acids can be administered to the subject (any mammalian recipient) using the same modes of administration that currently are used for gene therapy in humans (e.g., adenovirus-mediated gene therapy). Preferably, the Akt nucleic acid (contained in, or associated with, an appropriate vector) is administered to the mammalian recipient by intra-vascular or intra-muscular injection. A procedure for performing in vivo gene therapy for delivering a nucleic acid for performing ex vivo gene therapy is outlined in U.S. Pat. No. 5,399,346 and in exhibits submitted in the file history of that patent, all of which are publicly available documents. In general, ex vivo gene therapy involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Accordingly, the Akt nucleic acids of the invention can be delivered to the cells of the invention, ex vivo or in vivo, to treat excessive apoptotic cell-death. Numerous transfection and transduction techniques as well as appropriate expression vectors are well known to those of ordinary skill in the art, some of which are described in PCT application WO95/00654.

As an illustrative example, a vector containing an Akt nucleic acid is delivered to a site of increased apoptotic cell-death in a subject who is a candidate for such gene therapy. Then, the vector genetically modifies the cell in vivo with DNA (RNA) encoding an Akt polypeptide of the invention. Such genetically modified cells are expected to undergo apoptotic cell-death at a reduced rate and their survival in vivo is enhanced.

Another aspect of the invention includes a screening assay method for determining whether a putative therapeutic agent modulates apoptotic cell-death of cells. The method involves inducing apoptotic cell-death in a test sample containing one or more types of cells, contacting a putative inhibitory agent with the cells of the test sample under conditions to permit entry of the agent into the cell, determining a test sample index cell number, and comparing the test sample index cell number with a control index cell number of a control sample. The control sample contains cells that have been contacted with an Akt molecule under conditions to permit entry of the Akt molecule into the cells, and their index cell number is used as a reference number. The index cell number of the test sample as compared with the equivalent index cell number of the control sample is indicative of the inhibitory activity of the test agent in inhibiting death of the cells.

In one embodiment, the foregoing screening assay occurs in vitro. In preferred embodiments, the cells are selected from the group consisting of cardiac muscle cells (cardiomyocytes), skeletal muscle cells (skeletal myocytes) and vascular endothelial cells.

In another embodiment, the foregoing screening assay occurs in vivo. In preferred embodiments, the cells are cells of a subject from a tissue selected from the group consisting of myocardium, skeletal musculature and vascular endothelium.

Cell-death can be induced in a variety of ways well known in the art, including administration of glucocorticoids, reduction of hormone and/or growth factor levels, chemotherapy (toxic agents), mechanical injury and DNA damage.

The index cell number of the test sample as compared with the equivalent index cell number of the control sample serves as an indicator of the properties of the test agent in inhibiting death of the cells. An "index cell number" refers to a number of viable cells, to a number of dead cells, or to percentages of the foregoing numbers in relation to a total number of cells in a sample. Stains specific for either viable cells or dead cells may be used in order to facilitate the cell counting. Such stains are well known in the art, and exemplary ones are described below in the Examples. An index cell number, for example, of viable cells in the test sample, would be the "equivalent index cell number" of viable cells in the control sample.

The invention will be more fully understood by reference to the following examples. These examples, however, are merely intended to illustrate the embodiments of the invention and are not to be construed to limit the scope of the invention.

EXAMPLES

Example 1

Akt Controls Skeletal Myocyte Viability

During myogenesis, proliferating myoblasts withdraw from the cell cycle, acquire an apoptosis-resistant phenotype and differentiate into myotubes. Previous studies indicate that myogenic induction of the cyclin dependent kinase inhibitor p21 results in an inhibition of apoptotic cell-death in addition to its role as a negative cell cycle regulator. Here we demonstrate that the protein encoded by the Akt proto-oncogene is induced in C2C12 cells during myogenic differentiation with a corresponding increase in kinase activity. Expression of dominant negative forms of Akt induce cell-death during myogenesis, indicating that induction of Akt is essential for myocyte viability. Antisense oligonucleotides against p21 block cell cycle withdrawal, inhibit Akt induction, and enhance cell-death in myocyte cultures. Adenovirus-mediated transfer of Akt confers resistance to cell-death induced by p21 antisense. Collectively, these data indicate that cell cycle activity interferes with the myogenic induction of Akt, leading to apoptosis.

Materials and Methods:

Cell culture: C2C12 myoblasts (American Type Culture Collection, Manassas, Va.) were cultured as described in (Andrés, V. et al., *Mol. Cell. Biol.*, 1995, 15:3823-3829). Cells were maintained in growth media (Dulbecco's modified Eagle media [DMEM] supplemented with 20% fetal bovine serum). To induce differentiation, the media was switched to differentiation media (DMEM supplemented with 2% heat-inactivated horse serum) at 40-50% confluency. In some experiments, cells were shifted to DMEM containing 0.5% heat-inactivated horse serum or no serum.

Western immunoblot analysis: Cells were washed with PBS twice on ice and harvested by scraping. Cell lysates were prepared in cell lysis buffer (1% NP-40, 10% glycerol, 137 mM NaCl, 20 mM Tris-HCl pH7.4, 20 mM NaF, 2 mg/ml leupeptin, 1 mM PMSF) by rotating for 15 min at 4° C., followed by the centrifugation at 14,000 rpm for 10 min. Protein concentration was determined with a BCA kit (Pierce Chemical Co., Rockford, Ill.). Twenty mg of proteins were separated on an SDS-polyacrylamide gel and transferred to PVDF membrane (Millipore Corp., Bedford, Mass.). The membrane was blocked with T-PBS (1×PBS, 0.2% Tween) containing 5% dry milk, and incubated with primary antibody. After three washes with T-PBS, the blots were incubated with secondary antibody [donkey anti-rabbit (Amersham Corp., Arlington Heights, Ill.), or donkey anti-goat (Santa Cruz Biotechnologies, Inc., Santa Cruz, Calif.) IgG-conjugated with horse radish peroxidase] and developed by ECL detection system (Amersham Corp.). Anti-Akt, anti-p21, and anti-Cdk4 were purchased from Santa Cruz Biotechnologies, Inc., Santa Cruz, Calif.

In vitro kinase assay: Akt kinase assay was performed as described in (Franke, T. F., et al., *Cell* (1995) 81:727-736) with minor modifications. Briefly, 100 mg of protein in 500 ml of the cell lysis buffer, described above, was preincubated with protein G agarose for 30 min at 4° C. After centrifugation, anti-Akt or anti-HA antibody and protein G agarose (Boehringer Mannheim Biochemicals, Indianapolis, Ind.) were added to the supernatant in the presence of 2 mg/ml bovine serum albumin. Immunoprecipitation was performed at 4° C. for 2 hours. After washing twice with cell lysis buffer, once with $H_2O$, and twice with kinase buffer (20 mM HEPES pH7.2, mM $MgCl_2$, 10 mM $MnCl_2$), immunoprecipitates were incubated in 50 ml of kinase buffer containing 2 mg histone H2B (Boehringer Mannheim Biochemicals) and [$\gamma$-$^{32}$P] ATP (5 mM, 10 mCi) (DuPont-NEN, Boston, Mass.) at room temperature for 30 min. Kinase reactions were terminated by adding SDS-sample solution. After electrophoresis on 15% polyacrylamide gels, gels were dried and exposed to X-ray film.

Northern blot analysis: Northern blotting was performed as described in (Altomare, et al., *Oncogene*, 1995, 11:1055-1060). In brief, total RNA was prepared with acid guanidium thiocyanate-phenol-chloroform method (Chomczynski, P., et al., *Anal. Biochem.*, 1987, 162:156-159). Total RNA (25 mg) was separated in formaldehyde gel and transferred to nylon membrane Hybond N membrane (Amersham Corp.). After crosslinking by irradiation with ultraviolet light, the membrane was prehybridized in Rapid-hyb buffer (Amersham Corp.) for 2 hours at 65° C., followed by hybridization overnight. The probe was a cDNA fragment corresponding to the PH domain of mouse Akt which was radio-labeled with a random primer labeling kit (multiprime, Corp.) and purified with the Nick column (Pharmacia Biotech, Inc., Piscataway, N.J.). The membrane was washed, twice in 2×SSC solution containing 0.1% SDS at room temperature for 10 min, twice 2×SSC solution at 50° C. for 10 min, twice in 0.5×SSC solution containing 0.1% SDS at 65° C. for 10 min, and twice in 0.2×SSC solution containing 0.1% SDS at 65° C. for 10 min. The membrane was exposed to X-ray film.

Antisense oligonucleotide experiments: Antisense phosphorothioate oligonucleotides against p21 (5'-TGT CAG GCT GGT CTG CCT CC-3', SEQ ID NO. 7) and the control (5'-TGG ATC CGA CAT GTC AGA-3', SEQ ID NO. 8) were designed and were transfected into the cells with Lipofectin (Gibco BRL, Gaithersburg, Md.) method according to (Poluha, et al. *Mol. Cell. Biol.*, 1996, 16:1335-1341). Cells were cultured in growth media at a density of 3×10$^5$ cells in 100 mm dishes overnight. Cells were washed in differentiation media after the growth media was removed and exposed to oligonucleotide solution. The oligonucleotide solution was prepared by incubating oligonucleotides with 75 mg of Lipofectin in 1.5 ml of OptiMEM for 15 minutes at room temperature. Then the oligonucleotide-Lipofectin mixture was diluted with differentiation media and added to the cells. For cell survival analysis, cells were plated at a density of 1×10$^4$ cells in a 24 well dish. Treatment of oligonucleotides was performed as described above. Flow cytometry analyses were performed according to (Wang, et al., *Cancer Res.*, 1997, 57:351-354). In brief C2C12 cells were cultured in differentiation media with the antisense or control oligonucleotides mixed with Lipofectin, as described previously, for 24 hours. Cells were washed with PBS and fixed with 70% ethanol after washed with PBS. Samples were stained with propidium iodide. DNA content was measured using a FACScan flow cytometer (Becton Dickinson Immunocytometry Systems, San Jose, Calif.) according to (Wang, et al., *Cancer Res.*, 1997, 57:351-354).

Adenovirus vector construction and infection: The Adeno-Akt vector expresses a cDNA encoding mouse Akt protein fused to the hemagglutinin epitope (HA). Transgene expression is regulated by the cytomegalovirus promoter. Adeno-Akt was constructed according to (Becker et al., *Methods in Cell Biology*, Academic Press. New York, N.Y., 1994, 43:161-189.). In brief, HA-Akt fragment from pcDNA3-HA-Akt plasmid was inserted into the EcoR1/XbaI site of pACCMVpLpA plasmid. pACCMVpLpA-HA-Akt was co-transfected with pJM17 plasmid into 293 cells for homologous recombination to produce Adeno-Akt. Adeno-Akt was amplified in 293 cells and purified by ultracentifugation in the presence of CsCl. Recombinant adenovirus expressing β-galactosidase (Adeno-β-gal) has been described previously (Smith et al., *Genes Dev.*, 1997, 11:1674-1689). For transfection, C2C12 cells were incubated with the adenovirus at a multiplicity of infection (MOI) of 250 in growth media for 24 hours. Virus was removed when the media was replaced. Under these conditions, transfection efficiency was greater than 90%.

Plasmid transfection and cell viability analysis: The empty expression vector (pcDNA3), or the expression vector encoding wild-type Akt tagged with HA, or dominant negative forms of Akt (Akt [K179M] or Akt [T308A, S473A]) was co-transfected with an expression vector encoding enhanced green fluorescent protein (GFP) (Clontech Laboratories, Inc., Palo Alto, Calif.) at a ratio of 9:1 by the LipofectAmine method (Gibco BRL, Gaithersburg, Md.) according to the manufacturer's protocol. In brief, C2C12 cells were plated in 24-well plates overnight and incubated in a mixture of each individual plasmid (2 mg per well) and LipofectAmine (1:5 [wt:wt]) in growth media for 6 hours. After an 18 hour incubation in growth media, cells were changed to low-mitogen media. After incubating for 24 hours, cells were fixed with 3.7% formaldehyde and stained with Hoechst 33342. Floating and adherent GFP-positive cells with pyknotic or normal nuclei were determined by visual examination, and the fraction of the cells with pyknotic nuclei was calculated.

Statistical analyses: Differences between data groups were assessed for statistical significance using an unpaired t-test.

Results:

Akt upregulation during muscle differentiation: Changes in the level of Akt protein during murine C2C12 myogenesis were examined by Western immunoblot analysis. C2C12 myoblasts cultured in high-mitogen growth media expressed low levels of Akt protein, but Akt was markedly induced following exposure of cultures to low-mitogen differentiation media. C2C12 cells were cultured in growth media (GM) or in differentiation media (DM) for 24 hours (1 d) or for 48 hours (2 d). Cell lysates containing 20 mg protein were subjected to Western immunoblot analysis using anti-Akt, p21, and Cdk4 antibodies.

Northern blot analyses revealed that Akt mRNA is constitutively expressed during C2C12 differentiation and is not upregulated during myogenesis. Total RNAs were prepared from the C2C12 cells in GM, or in DM for 24 hours or for 48 hours. Northern blot analysis was performed using a cDNA probe to the PH domain of Akt. The 28S RNA band is shown to indicate equal loading of the gel. Akt mRNA is also not upregulated in MyoD-transformed 10T1/2 cells when they are exposed to differentiation media. In contrast, the Akt-related gene Akt2 is upregulated by myogenic differentiation at the level of mRNA (Altomare, et al., *Oncogene*, 1995, 11:1055-1060; Altomare et al., *Oncogene*, 1998, 16: 2407-2411). Upregulation of Akt2 protein was also detected in the C2C12 cultures, but in contrast to Akt, Akt2 upregulation was less pronounced. Thus, efforts were primarily directed toward understanding the functional significance of Akt induction during myogenic differentiation.

H2B kinase activity in Akt immunoprecipitates was analyzed in extracts prepared from cultures exposed to growth and differentiation media. The data show that Akt kinase activity is induced during myogenesis. Cell lysates were prepared from C2C12 cells cultured in growth media or in differentiation media for 48 hours. Kinase activity was determined in anti-Akt immunoprecipitates using histone H2B as a substrate. Consistent with previous reports (Guo, et al., *J. Biol. Chem.*, 1995, 270:6729-6733; Halevy, et al., *Science*, 1995, 267:1018-1021; Missero, et al., *Proc. Natl. Acad. Sci. USA*, 1995, 92:5451-5455), the cdk inhibitor p21 was induced by differentiation, while the levels of cdk4 did not change. Akt activity was low in the proliferating myoblasts cultures, but activity was induced in cultures exposed to differentiation media. The increase in Akt kinase activity appeared to parallel the increase in Akt protein.

Figure 1B:
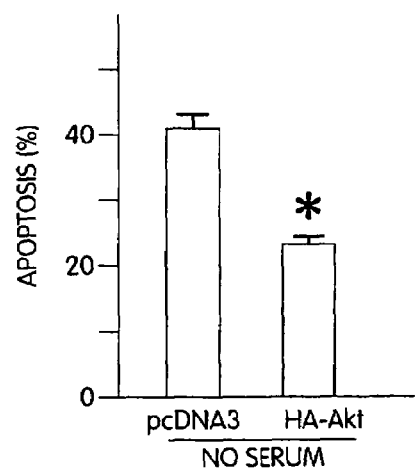

Akt controls myocyte viability: Two dominant-negative forms of Akt were analyzed to assess the role of Akt in myocyte survival during differentiation. The mutant Akt [K179M] has a mutation in the ATP-binding site and is catalytically inactive (Bellacosa et al., *Oncogene*, 1993, 8:745-754), while the mutant Akt [T308A, S473A] has alanine substituted for serine/threonine at the indicated residues and cannot be activated by phosphorylation (Alessi et al., *EMBO J.*, 199615:6541-6551). Each mutant Akt expression plasmid was co-transfected with a vector expressing a green fluorescent protein (GFP) into C2C12 cells (Dudek et al., *Akt. Science*, 1997, 275:661-665). Transfected cultures were incubated in growth media for 18 hours and then in DMEM with 0.5% horse serum for 24 hours. Apoptosis was assessed in the cultures by analyzing the fraction of floating and adherent GFP-positive cells with pyknotic nuclei following staining with Hoechst. Pyknotic, Hoescht 33342-stained nuclei that correspond to the floating GFP-positive cells in cultures transfected with K179M Akt. In contrast, cultures co-transfected with an expression plasmid encoding wild-type. Akt revealed a high frequency of adherent GFP-positive cells with normal appearing nuclei. Co-transfection with either dominant-negative Akt construct markedly increased the fraction of GFP-positive cells that were floating and contained pyknotic nuclei. Cells were co-transfected with empty vector (pcDNA3) or plasmids expressing the dominant negative forms of Akt using the LipofectAmine method. After transfection, cells were incubated in growth media for 18 hours, then in DMEM containing 0.5% horse serum. After 24 hour incubation, cells were fixed and stained with Hoechst as described in Methods. The adherent and floating transfected GFP-positive cells were scored for normal or pyknotic nuclei. Data are shown as mean +/−S.E.M. (*$p<0.01$) (FIG. 1A). In contrast, forced expression of wild-type Akt in the co-transfection assay reduced the fraction of floating GFP-positive cells with pyknotic nuclei when cultures were incubated in serum-free media (FIG. 1B). Cells were co-transfected with the indicated expression plasmids and the GFP expression plasmid. After 18 hour incubation in growth media, the media was changed to DMEM without serum. After 24 hour incubation, the transfectants were scored as described in A. Data are shown as mean +/−S.E.M (*p<0.01) (FIG. 1B). Collectively, these data suggest that Akt upregulation is essential for full myocyte viability during differentiation and that elevated Akt levels are sufficient to confer resistance to apoptosis under these conditions.

p21-mediated cell cycle withdrawal is required for Akt induction and cell survival: To investigate the relationship between p21 and Akt in myocytes, we investigated the effects of p21 antisense oligonucleotides on cell cycle, apoptosis and Akt induction. C2C12 cultures were treated with p21 antisense or control oligonucleotides and induced to differentiate. Western immunoblot analysis of cultures harvested after 24 hours of treatment revealed that the p21 antisense oligonucleotides markedly inhibited the induction of p21. C2C12 cells were cultured in standard differentiation media (−) or in differentiation media containing Lipofectin with the p21 antisense oligonucleotides (AS) or control oligonucleotides (Cont) for 24 hours. After 24 hour incubation, cells were harvested and cell lysates (20 mg protein) were immunoblotted with anti-Akt, anti-p21, and anti-Cdk4 antibodies. These experiments also revealed a statistically significant reduction in Akt expression accompanying the reduction in p21 expression. The antisense oligonucleotides had no significant effect on cdk4. The intensities of the Akt and Cdk4 bands in immunoblots from five independent experiments were quantified by gel densitometer.

Flow cytometric analyses were performed to determine the effect of the p21 antisense oligonucleotides on cell cycle progression during differentiation. As shown below in Table 1, cultures treated with p21 antisense oligonucleotides for 24 hours had a greater percentage of cells in the S and G2/M phases of the cell cycle than cultures treated with control oligonucleotides or with differentiation media alone. These data provide causal evidence that p21 induction is critical for cell cycle exit during myogenic differentiation.

TABLE 1

Antisense oligonucleotides against p21 mRNA block cell cycle exit upon myogenic differentiation.

| Addition[a] | Cell cycle phase[b] | | |
|---|---|---|---|
| | $G_0/G_1$ | S | $G_2/M$ |
| None | 62 | 27 | 11 |
| p21-AS | 38 | 45 | 17 |
| Control | 67 | 25 | 8 |

[a]C2C12 cells were cultured in differentiation media in the presence or absence (none) of 0.5 mM phosphorothioate antisense oligonucleotides to p21 (p21-AS) or control oligonucleotides for 24 hours.
[b]DNA content was determined by FACS analysis.

Induction of p21 coincides with the acquisition of an apoptosis-resistant phenotype, and forced expression of p21 can block apoptosis in cultures of C2C12 myocytes (Wang, J., et al., Cancer Res., 1997, 57:351-354; Wang, J., et al., Science, 1996, 273:359-361.). Thus, we analyzed the effects of the p21 antisense oligonucleotides on myocyte survival. The cells were plated and transfected with the oligonucleotides. C2C12 cells were cultured in standard differentiation media or in differentiation media containing lipofectin with the indicated oligonucleotides for 24 or 48 hours. Markedly enhanced cell-death was observed in cultures treated with p21 antisense oligonucleotides than in control cultures. The frequency of cell-death was dependent on the dose of p21 antisense oligonucleotides, and cell-death was most notable after 48 hours in differentiation media. Collectively, these data indicate that p21-mediated cell cycle withdrawal is essential for cell survival during myogenesis.

Figure 2A:
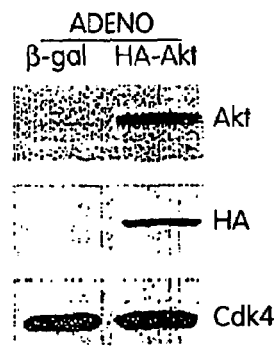
FIG. 2. Graph showing that forced Akt expression promotes the survival of mitotic myocytes. (A) Myoblasts infected with Adeno-Akt express the Akt transgene as indicated by Western immunoblot analysis using either anti-Akt or anti-HA antibodies. (B) Anti-Akt and anti-HA immunoprecipitates from Adeno-Akt-infected myoblast cultures also contained appreciable levels of H2B kinase activity, indicating that the transgene produces functional Akt protein. (C) Cultures infected with Adeno-Akt displayed significantly less cell-death than control cultures.
Figure 2B:
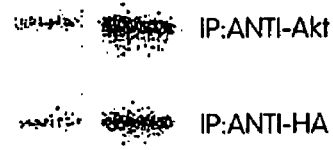
Figure 2C:
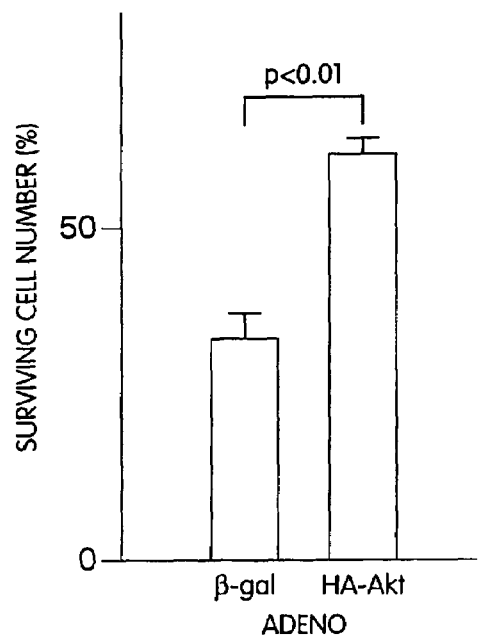

Adenovirus-mediated Akt gene transfer can protect mitotic cells from death during myogenic so differentiation: To test whether forced Akt expression can rescue myocytes from the high frequency of cell-death that occurs when they are blocked from cell cycle exit, a replication-defective adenoviral construct expressing wild-type Akt fused to the hemagglutinin (HA) epitope was constructed (Adeno-Akt). Control cultures were infected with an adenoviral vector expressing β-galactosidase (Adeno-13-gal), which does not affect apoptosis in C2C12 cells during myogenic differentiation (Wang, J., et al., Cancer Res., 1997, 57:351-354). Myoblasts infected with Adeno-Akt express the Akt transgene as indicated by Western immunoblot analysis using either anti-Akt or anti-HA antibodies (FIG. 2A). Under these transfection conditions, the overall level of adenovirus-mediated Akt expression is approximately 5- to 10-fold in excess of the induced level of endogenous Akt in differentiated myocyte cultures as assessed by Western blot analyses. Anti-Akt and anti-HA immunoprecipitates from Adeno-Akt-infected myoblast cultures also contained appreciable levels of H2B kinase activity, indicating that the transgene produces functional Akt protein (FIG. 2B). As shown above, antisense oligonucleotides to p21 inhibit cell cycle withdrawal during myogenesis, and these cultures eventually undergo apoptosis at a high frequency. To test whether forced Akt expression could promote cell viability under these conditions, cells were infected with adenoviral constructs prior to exposure to the p21 antisense oligonucleotides in differentiation media. C2C12 cells were cultured in growth media and infected with Adeno-Akt or Adeno-β-galactosidase at MOI of 250 for 24 hours. Cultures were then transferred to differentiation media in the presence of 0.5 mM p21 antisense oligonucleotide for 36 hours. Cell number was determined by counting with a hemacytometer. Cell numbers are normalized to parallel cultures transfected with the adeno-β-galactosidase vector in differentiation media in the absence of antisense oligonucleotides. Data are shown as mean +/−S.E.M. (n=4). Cultures infected with Adeno-Akt displayed significantly less cell-death than control cultures (FIG. 2C). These data show that Akt is effective in protecting mitotic cells against death during the differentiation process.

Example 2

Akt Mediates Cytoprotection of Endothelial Cells by Vascular Endothelial Growth Factor Vascular endothelial growth factor (VEGF) is a key regulator of angiogenesis that functions through its ability to promote endothelial cell growth and survival. In this study, we examined the role of the protein kinase Akt/PKB in VEGF-mediated endothelial cell survival. VEGF protection of mitogen-deprived human umbilical vein endothelial cells (HUVECs) correlated with the activation of Akt, but not Akt2. Wortmannin, a PI 3-kinase inhibitor, so abrogated the survival effects of VEGF and blocked Akt induction. Transfection of a dominant negative Akt mutant decreased HUVEC viability in the presence of VEGF. Conversely, adenoviral transduction of wild-type Akt promoted the cell survival effects of VEGF with a corresponding increase in Akt kinase activity. These data suggest that Akt activation is a critical step in VEGF-mediated endothelial cell survival.

Materials and Methods:

Reagents, Plasmids and Cell Culture: Wortmannin was purchased from the Sigma Chemical Co., St. Louis, Mo. Anti-Akt2 antibodies, and Akt plasmids were a gift from Dr. J. Testa (Fox Chase Cancer Center, Philadelphia, Pa.). Recombinant human VEGF was the 165 amino acid isoform. HUVECs were cultured in Dulbecco's modified Eagle medium (DMEM) for serum deprivation and stimulated with VEGF as described by (Spyridopoulos, I., et al., *J. Mol. Cell. Cardiol.*, 1997, 29:1321-1330).

Akt kinase assay was performed as described in Example 1.

Cell viability assay: Cells were plated on 24 well dishes at a density of $4 \times 10^4$ cells/well. After overnight incubation, the media was changed to DMEM containing 20% fetal bovine serum (FBS) or the indicated concentrations of VEGF for 21 hrs. Cells were then washed with PBS, harvested by trypsinization, and viability was determined by the Trypan-blue exclusion assay (Messner, P., et al., *J. Cell. Biol.*, 1992, 119:1669-1680; Zhou, S., et al., *Natl. Acad. Sci. USA*, 1997, 94:11345-11350).

Adenoviral construction and transfection was also performed as described in Example 1.

Plasmid transfection and cell viability assay: Plasmid transfection was accomplished using the Superfect reagent (Qiagen, Santa Clarita, Calif.) according to the manufacturer's protocol with minor modifications. In brief, HUVECs were plated in 24 well dishes at a cell density of $4 \times 10^4$ overnight. Plasmid mixtures (60 ml containing 1.6 mg of pcDNA3 expressing dominant negative Akt (K179M) or pcDNA3 empty vector, and 0.4 mg pCMV-β-galactosidase) were incubated for 10 min. at room temperature with 10 ml of Superfect. The plasmid-Superfect solution was then diluted to 350 ml with complete media (DMEM plus 20% fetal bovine serum) and added to the HUVEC cultures for 1 hr. Cells were then washed with complete media 5 times and incubated in the same media for 24 hrs. Cells were then changed to serum-free DMEM with or without VEGF (25 ng/ml) for 21 hrs. After 21 hour incubation, the number of surviving β-galactosidase-positive cells was determined by staining with X-gal (Miura, M., et al., *Cell*, 1993, 75:653-660; Boyd, J., et al., *Oncogene*, 1995, 11:1921-1928; Chittenden, T., et al., *EMBO J.*, 1995, 14: 5589-5596).

Results

VEGF promotes HUVEC survival: Consistent with previous reports (Gerber, H., et al., *J. Biol. Chem.*, 1998, 273:13313-13316; Levkau, B., et al., *Mol. Cell.*, 1998, 1:553-563; Scatena, M., et al., *J. Cell. Biol.*, 1998, 141:1083-1093), serum-deprivation induces endothelial cell-death. Cells were plated in 24 well dishes overnight and then cultured in DMEM containing 20% fetal bovine serum (open bar) or the indicated concentrations of VEGF (closed bars). After 21 hrs. in culture, cell viability was determined by the Trypan-blue exclusion assay (Mesner, P., et al., *J. Cell. Biol.*, 1997, 119:1669-1680; Zhou, S., et al., *Proc. Natl. Acad. Sci., USA*, 94:11345-11350) performed in quadruplicate. Serum-deprivation for 21 hrs. resulted in 50% to 80% decreases in HUVEC viability depending on the preparation and passage number, where higher passage cells (passage 4 or 5) were more sensitive to death than lower passage cells. It has been reported that VEGF inhibits HUVEC apoptosis induced by serum deprivation (Gerber, H., et al., *J. Biol. Chem.*, 1998, 273:13313-13316). FIG. 6B shows that wortmannin abrogates the cytoprotection of VEGF. Cells were plated overnight and then cultured in DMEM containing the indicated concentrations of wortmannin in the presence (closed bars) or absence (open bar) of VEGF (100 ng/ml). After 21 hours culture, viability was determined by the Trypan-blue exclusion assay performed in quadruplicate. Under the conditions of our assays, 100 ng/ml VEGF completely reversed cell loss induced by serum-deprivation. Inclusion of 200 nM wortmannin in the media blocked the ability of VEGF to rescue HUVEC cultures from cell-death. Partial inhibition of VEGF-mediated HUVEC survival occurred when cultures were incubated with 10 or 50 nM wortmannin.

VEGF activates Akt in HUVEC cultures: To determine whether VEGF regulates the activity of Akt family proteins in endothelial cells, HUVEC cultures were incubated in serum-free DMEM with or without VEGF (100 ng/ml). The kinase activities of Akt and the Akt-related protein Akt2 were determined in lysates immunoprecipitated with specific anti-Akt or anti-Akt2 antibodies. VEGF activated Akt kinase activity in mitogen-deprived HUVEC cultures, but little or no activation of Akt2 by VEGF was detected. Serum-deprived HUVEC cultures were incubated in the presence or the absence of VEGF (100 ng/ml) for 15 min. Cell lysates were prepared and immunoprecipitated with anti-Akt antibodies, anti-Akt2 antibodies, or none. Kinase activities were measured with histone H2B as a substrate.

Since Akt is regulated by PI 3-kinase in other cell types (Franke, T., et al., *Cell*, 1995, 81:727-736), we investigated the effects of wortmannin on Akt activation by VEGF. A 30 min preincubation with 200 nM wortmannin blocked VEGF-induced Akt activity. HUVEC cultures were preincubated in serum-free DMEM in the presence or absence of wortmannin (200 nM) for 30 min. Cells were then stimulated with VEGF (100 ng/ml) for 15 min. Cell lysates were prepared and immunoprecipitated with anti-Akt antibodies. As a control, immunoprecipitation was performed in the presence of the competitor oligopeptides. Kinase activities were measured with Histone H2B as a substrate. Collectively, these data show that HUVEC survival correlates with Akt activity.

A dominant-negative mutant of Akt inhibits the cell survival effects of VEGF: A dominant-negative mutant of Akt was analyzed to assess the role of Akt in VEGF-mediated HUVEC survival. The mutant Akt[K179M] has a mutation in the ATP-binding site and is catalytically inactive (Bellacosa., et al., *Oncogene*, 1993, 8:745-754). A cell-death assay was performed using an expression plasmid encoding Akt [K179M] or an empty expression vector transfected in combination with a β-galactosidase expression plasmid. Cell viability was assessed by determining the number of surviving β-galactosidase-positive cells (Miura, M., et al., *Cell*, 1993, 75:653-660; Boyd, J., et al., *Oncogene*, 1995, 11:1921-1928; Chittenden, T., et al., *EMBO J.*, 1995, 14: 5589-5596). In this assay, HUVEC cultures were incubated in serum-free media in the presence or absence of 25 ng/ml VEGF. VEGF increased the number of surviving β-galactosidase positive cells transfected with control plasmid by a factor of 3. A plasmid vector expressing Akt[K179M] (D.N.) or empty vector (Cont) were co-transfected with a β-galactosidase expressing vector. After 24 hrs. recovery in complete media, cultures were switched to serum-free DMEM for 21 hrs. in the absence or presence of VEGF (25 ng/ml). The number of surviving β-galactosidase-positive cells was determined by visual inspection. Assays were performed in quadruplicate. In the absence of VEGF, the Akt [K179M]

expression plasmid did not diminish the number of surviving β-galactosidase positive cells. However, Akt [K179M] decreased HUVEC viability in the presence of VEGF.

Figure 3A:
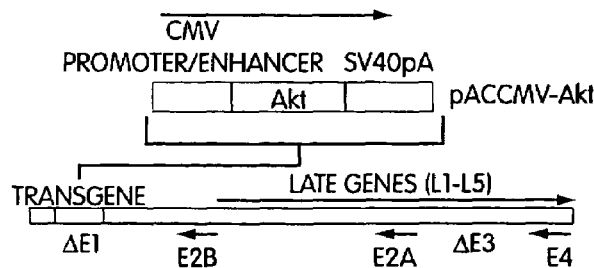
FIG. 3. Adenoviral transfection of Akt promotes the VEGF-mediated cell survival of HUVEC cultures; (A) the structure of replication-defective adenoviral vector expressing the Akt cDNA; (B) adenoviral mediated expression of Akt enhanced VEGF-induced cell survival. Data were shown as the mean +/−S.E.M. Control cultures (closed circles) received vehicle alone. were infected with an adenoviral vector expressing β-galactosidase (Ad-β-gal), which does not affect endothelial cell viability under the conditions of our assay.
As shown in FIG. 3B, adenoviral transfection of Akt markedly augmented VEGF-induced endothelial cell survival. In brief, HUVECs were cultured in 24 wells (Falcon) and infected with adenoviral vector expressing Akt (Ad-Akt) or β-galactosidase (Ad-β-gal) at a MOI of 50. After 24 hour incubation, the medium was changed to DMEM containing the indicated concentrations of VEGF. After 21 hours culture, viable cells were counted.
Figure 3B:
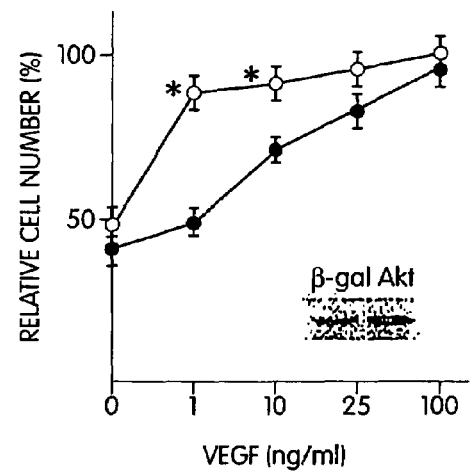

Adenoviral transfection of Akt promotes the endothelial cell viability in response to VEGF: To further explore the functional significance of VEGF-induced Akt activity in endothelial cell survival, a replication-defective adenoviral vector expressing wild-type Akt (Ad-Akt) was constructed (FIG. 3A). Control cultures were infected with an adenoviral vector expressing β-galactosidase (Ad-β-gal), which does not affect endothelial cell viability under the conditions of our assay. As shown in FIG. 3B, adenoviral transfection of Akt markedly augmented VEGF-induced endothelial cell survival. In brief, HUVECs were cultured in 24 wells (Falcon) and infected with adenoviral vector expressing Akt (Ad-Akt) or β-galactosidase (Ad-β-gal) at a MOI of 50. After 24 hour incubation, the medium was changed to DMEM containing the indicated concentrations of VEGF. After 21 hours culture, viable cells were counted. Assays were performed in quadruplicate. Data were shown as the mean +/−S.E.M. Inset: HUVEC cultures were infected with Ad-β-gal (β gal) or Ad-Akt (Akt) and incubated for 24 hours. After 30 min. serum starvation, cells were treated with 1 ng/ml of VEGF for 15 min. The cell lysates were prepared and immunoprecipitated with anti-Akt antibodies. The kinase activities were measured as described in Materials and Methods. Cultures infected with Ad-Akt displayed 75 and 65% less cell-death than control cultures at 1 and 10 ng/ml, respectively, while no decrease in cell-death was detected in the cultures exposed to serum-free media in the absence of VEGF. As anticipated, adenoviral transfection of Akt also enhanced Akt kinase activity (FIG. 3B, inset). Akt immunoprecipitates prepared from Ad-Akt-infected HUVEC cultures exhibited greater kinase activity than control cultures when exposed to 1 ng/ml VEGF, the concentration of factor that produced the greatest difference in survival between test conditions. These data show that forced Akt expression can enhance the sensitivity of endothelial cells to VEGF survival signals.

Example 3

Akt Activation is Required for Insulin-Like Growth Factor-1 Mediated Survival of Cardiac Myocytes Insulin-like growth factor-1 (IGF-1) functions as a cytoprotective factor for cardiac myocytes. In the present study, we investigated the role of the Akt protein kinase in IGF-1-mediated cardiac myocyte survival. IGF-1-mediated protection of serum-deprived cardiac myocytes was abrogated by the phosphatidylinositol 3-kinase (PI 3-kinase) inhibitor wortmannin. Cytoprotection correlated with the wortmannin-sensitive induction of Akt protein kinase activity, a downstream target of PI 3-kinase. To analyze the cytoprotective effects of Akt, adenoviral vectors expressing wild-type, dominant-negative, and constitutively active Akt were constructed. Infection of cardiac myocytes with the adenoviral vector expressing dominant-negative Akt blocked IGF-1-induced survival, demonstrating that Akt activation is essential for cardiomyocyte survival under these conditions. In contrast, infection with the adenoviral construct expressing wild-type Akt enhanced IGF-1-mediated myocyte survival, while constitutively active Akt inhibited apoptsosis in the absence of IGF-1. Collectively, these data indicate that Akt activation is a step feature in the transduction of IGF-1 survival signals in cardiac myocytes.

Materials and Methods:

Reagents and Antibodies:

IGF-1 was purchased from Gibco BRL. Anti-hemagglutinin epitope (Anti-HA) antibody (clone 12CA5) and protein G-agarose were purchased from Boehringer Mannheim Biochemicals, Indianapolis, Ind. Peroxidase conjugated anti-mouse IgG was obtained from Amersham Corp.

Cell culture: Primary cultures of neonatal cardiac myocytes were prepared as described in (Simpson P, and Savion S, Circ Res, 1982, 50:101-116.). In brief, the ventricles of 1 or 2-d-old Sprague Dawley rats were digested with collagenase and trypsin (Sigma Chemical Co.). Cultures were enriched with cardiac myocytes by preplating for 60 min to eliminate fibroblasts. Non-attached cells were suspended in medium-199 (M−199) (Gibco BRL) supplemented with 10% heat inactivated fetal calf serum (FCS). Over 90% of the cells were identified as cardiac myocytes by immunocytochemistry with anti-sarcomeric α-actinin (Sigma Chemical Co.). Attached cells were passaged once and used as the non-cardiac myocyte fraction. Cells were pretreated with wortmannin for 30 min and incubated in the medium containing wortmannin in the presence or absence of IGF-1. Dimethyl sulfoxide (Sigma Chemical Co.) was used as the vehicle for the wortmannin at concentration of 0.1% (vol/vol). Control cultures received vehicle alone.

Akt activity assay: Akt kinase assay was performed as described in the previous examples. Cells were treated with IGF-1 as described below.

Western-blotting: Western-blotting was performed as described in the previous examples.

Trypan-blue exclusion assay: Cell viability was determined using the trypan-blue exclusion assay (Messner, P., et al., J. Cell. Biol., 1992, 119:1669-1680; Zhou, S., et al., Natl. Acad. Sci. USA, 1997, 94:11345-11350). Neonatal rat cardiac myocytes were cultured at a density of $2\times10^4/100$ μl in 96 well dishes. Cells were washed with PBS once and harvested by treatment with 25 μl of trypsin-EDTA. Proteolysis was stopped by adding a solution containing an equal amount of trypan blue solution and media containing 20% FCS. Thereafter, viability was scored by determining the fraction of cells that excluded trypan blue.

Adenoviral constructs: Wild-type and dominant-negative forms of human Akt were tagged with hemagglutinin epitope (HA) and constructed as described in the previous examples.

DNA fragmentation assay: DNA fragmentation analysis was performed as described previously (Wang J and Walsh K, Science, 1996, 273:359-361) with modification. Briefly, cardiac myocytes were plated at density of $2\times10^6$ cells/100 mm dish. Cells were infected with adenovirus vectors and cultured under various conditions for 48 hours. Thereafter, cells were suspended in 200 μl of PBS containing proteinase K, RNaseA, and 1% SDS and incubated at 37° C. for 30 min. NaI solution (300 μl, 6M NaI, 13 mM EDTA, 10 mg/ml glycogen, 26 mM Tris HCl (pH 8.0) was added and cell lysates were incubated at 60° C. for 15 min. DNA was precipitated by adding 500 μl of 100% isopropanol. After incubated at room temperature for 15 min, insoluble DNA was precipitated by centrifugation at 15000 rpm for 15 min. DNA (10 μg/lane) was analyzed by electrophoresis on a 15% agarose gel.

Results

IGF-1 protects cardiac myocytes from death under conditions of serum deprivation: To document the cytoprotective effects of IGF-1 under the conditions of our assays, neonatal rat cardiac myocytes were cultured in the serum-free media in the presence or absence of IGF-1, and cell viability was determined by trypan-blue exclusion at various time points. Cells were plated and incubated in M-199 containing 10% FCS. After overnight incubation, cell number was determined (100%). Cardiac myocytes were incubated with or without 50 ng/ml of IGF-1 under serum-depleted condition for indicated duration and counted in number with trypan-blue exclusion assay. All assays were performed in quadruplicates. In the presence of IGF-1, cardiac myocyte viability was sustained for more than 48 hours. In the absence of IGF-1, cardiac myocyte cultures displayed a time-dependent decrease in viability with greater than a 50% loss of live cells by 72 hrs. Compared with myocytes, the passaged non-myocyte cells (fibroblasts) prepared from neonatal heart were resistant to death induced by serum deprivation. Non-myocytes were plated and incubated as described above. After 72 hour incubation with (+) or without (−) IGF-1, viable cells were counted with trypan-blue exclusion assays. All assays were performed in quadruplicates. Data were shown as the mean +/−S.E.M. The insensitivity of cardiac fibroblasts to serum deprivation-induced cell death has been reported previously (Sheng Z, et al., *J Biol Chem.* 1997, 272:5783-5791).

Cytoprotection was dependent on the dose of IGF-1 in the culture media. Cardiac myocytes were plated overnight and then cultured in the serum-depleted medium containing various concentrations of IGF-1. After 72 hours in culture, cell viability was determined by the trypan-blue exclusion assays. Assays were performed in quadruplicates. IGF-1-induced cytoprotection was abrogated by treatment with 200 nM wortmannin, suggesting that the survival effects of IGF-1 is regulated by the effector protein(s) downstream of PI 3-kinase. Cardiac myocytes were plated overnight. After pretreatment with wortmannin for 30 min, cells were cultured in M199 containing the indicated concentrations of wortmannin in the presence or absence of IGF-1 (50 ng/ml). After 72 hour culture, viable cells were determined in number with trypan-blue exclusion assay performed in quadruplicates. In the absence of IGF-1, wortmannin had no effect on cardiomyocyte viability.

Wortmannin-sensitive activation of Akt by IGF-1 in cardiac mvocytes: Since Akt is reported to act downstream of PI 3-kinase in many cell types (include references in other cell types (Oh H, et al., *J Biol Chem*, 1998, 273:9703-9710), the affect of IGF-1 on Akt protein kinase activity of Akt was assessed. Akt activity was determined in cultures of serum-deprived cardiac myocytes in the presence or absence of IGF-1. Cell lysates were prepared as described in Materials and Methods and immunoprecipitated with anti-Akt antibody in the presence or absence of the immunogenic competitor peptides. Akt activity in the immunoprecipitated material was assayed using histone H2B as substrate. Serum-deprived neonatal cardiac myocytes were incubated with or without 50 ng/ml of IGF-1 for 15 min. Cell lysates were prepared as described in Materials and Methods and immunoprecipitated with anti-Akt antibody in the presence or absence of competitive peptides (Comp.) Akt activities in immunoprecipitates were measured with histone H2B as a substrate. IGF-1 induced the phosphorylation of histone H2B. The IGF-1-induced kinase activity is attributable to Akt since kinase activity was not detected in response to IGF-1 when immunoprecipitated in the presence of the immunogenic competitor peptide.

The effects of wortmannin on IGF-1-induced Akt activity was also analyzed. Cells were treated with or without IGF-1 (50 ng/ml) in the presence or absence of 200 nM wortmannin. Cell lysates were prepared as described in Materials and Methods and immunoprecipitated with anti-Akt antibody. Kinase activities were measured as described in Materials and Methods. Inclusion of 200 nM wortmannin in the culture media completely blocked IGF-1-activated Akt kinase activity. These data suggest that Akt acts downstream of PI 3-kinase in response to IGF-1.

Adenoviral transfection of wild-type and mutant forms of Akt in cardiac myocytes: To determine the functional significance of Akt activation in the IGF-1-stimulated cardiac myocyte cultures, replication-defective adenoviral vectors expressing wild and mutant forms of Akt were constructed. The mutant Akt [T308A, S473A] has alanine substituted for serine or threonine at the indicated residues and cannot be activated by phosphorylation (Alessi D R, et al., *J Biol Chem,* 1995, 270:27489-27494). Both wild-type and mutant Akt were fused to the hemagglutinin (HA) epitope. Cardiac myocytes were infected overnight with adenovirus vectors at multiplicity of infection (m.o.i.) of 25, and expression of the exogenous Akt proteins were analyzed by Western immunoblot with anti-HA antibody. Expression of the transgene products was detected in the cardiac myocytes transfected with the Akt adenoviral constructs, but not in parallel cultures infected with a control adenovirus vector expressing β-galactosidase (β-gal).

To analyze the kinase activities of adenovirally-encoded Akt proteins, parallel serum-deprived cultures were incubated in the presence or absence of 50 ng/ml of IGF-1 for 15 min. Cell extracts were then immunoprecipitated with anti-HA antibody and the H2B protein kinase activity of the immunoprecipitate was determined. Akt protein kinase activity was detected in cells infected with the wild-type Akt vector in the presence, but not absence, of IGF-1 stimulation. In contrast, the vector expressing dominant-negative Akt was inactive in the presence or absence of IGF-1, though mutant Akt protein was expressed).

Figure 4:
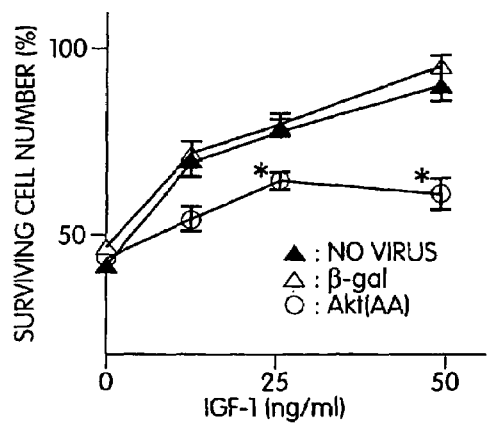
FIG. 4. Dominant-negative Akt inhibits IGF-1-mediated myocyte survival.

Adenovirus transduction of dominant-negative Akt inhibits IGF-1-mediated cardiac myocyte survival: Cardiac myocyte cultures were infected with an adenoviral vector expressing dominant-negative Akt mutant (Akt(AA)) to test whether Akt is essential for IGF-1-mediated survival. Cells were mock-infected (closed triangles) with adenovirus vectors expressing Akt(AA) (open circles) or β-gal (open triangles) at an m.o.i. of 25, overnight. After infection, media was removed and cells were in serum-free media in the presence or absence of the indicated concentrations of IGF-1 for 72 hours (FIG. 4). Viable cell number was determined by the trypan-blue exclusion assay performed in quadruplicate. Surviving cell number is expressed relative to the initial cell number. Data were shown as the mean +/−S.E.M. *$p<0.05$ by unpaired t-test. In the absence of IGF-1, the dominant-negative Akt construct did not affect cardiac myocyte survival, but it largely eliminated the increase in cell survival resulting from the inclusion of 25 or 50 ng/ml IGF-1 in the culture medium. In contrast, the control adenoviral construct expressing P-gal had no detectable effect on cardiac myocyte viability.

Figure 5:
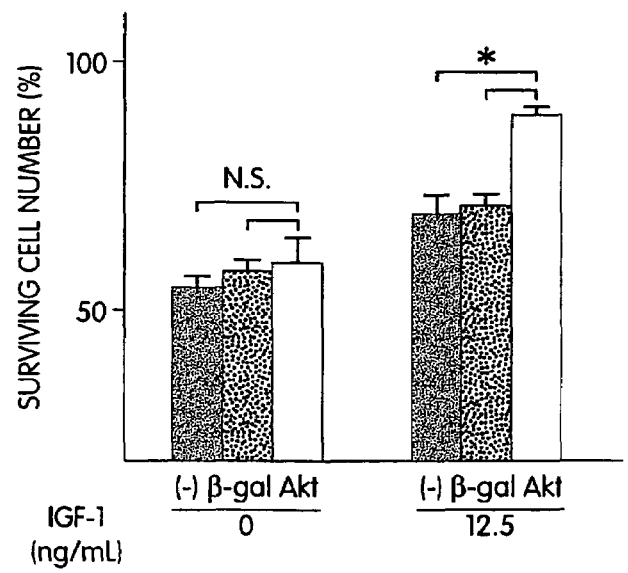
FIG. 5. Overexpression of wild-type Akt facilitates myocyte survival in response to IGF-1.

Transduction of wild-type Akt enhances IGF-1 survival signals: To investigate the consequences of Akt overexpression on cardiac myocyte survival, serum-deprived cultures were transfected with adenoviral vectors expressing wild-type Akt or β-gal for overnight and cultured in the absence or presence of IGF-1 for 72 hours. Cells were mock-infected (black columns) or infected with adenovirus vectors expressing β-gal (gray columns) or wild-type Akt (white columns) (FIG. 5). Parallel cultures were then incubated in serum-free media in the presence or absence of 12.5 ng/ml IGF-1 for 72 hours. Cell viability was determined by the Trypan-blue exclusion assay performed in quadruplicate. Surviving cell number is expressed as a percentage of the initial cell number. Data were shown as the mean +/−S.E.M. *p<0.05 by unpaired t-test. As shown in FIG. 5, overexpression of wild-type Akt had no significant effect on survival in the absence of IGF-1. In the presence of a sub-saturating concentration of IGF-1, cell survival was promoted by Akt overexpression, but the β-gal-expressing construct had no effect on viability. However, overexpression of Akt had little or no effect on cell viability at higher IGF-1 concentrations. Therefore, it appears that adenovirus-mediated Akt gene transfer enhances the survival effects of IGF-1, indicating that Akt is a limiting factor in survival of cardiac myocytes under these conditions.

Transduction of constitutively-active Akt promotes cardiac myocyte survival in the absence of IGF-1: The adenoviral vector expressing constitutively active Akt also inhibited cardiomyocyte death as indicated by its ability to decrease the cleavage of DNA into 180 base pair fragments.

Example 4

Akt Promotes Survival of Cardiomyocytes In Vitro and Protects Against Ischemia-Reperfusion Injury in Mouse Heart In Vivo To examine the functional consequences of Akt activation in cardiomyocyte survival, replication-defective adenoviral constructs expressing wild-type, dominant-negative and constitutively-active Akt genes were constructed. Transduction of dominant-negative Akt blocked IGF-1-induced survival, but had no effect on cardiomyocyte survival in the absence of IGF-1. In contrast, transduction of wild-type Akt enhanced cardiomyocyte survival at sub-saturating levels of IGF-1, while constitutively-active Akt protected cardiomyocytes from apoptosis in the absence of IGF-1. Following transduction into the mouse heart in vivo, constitutively-active Akt protected against myocyte apoptosis in response to ischemia-reperfusion injury. These data are the first documentation that Akt functions to promote cellular survival in vivo and they indicate that the activation of this pathway may have utility in promoting myocyte survival in the diseased heart.

Materials and Methods:

Reagents, cell culture and Akt assays: IGF-1 were purchased from Gibco BRL. Wortmannin was obtained from Sigma. Anti-Akt antibody and its corresponding immunogenic peptide came from Santa Cruz Biotechnology. Anti-HA antibodies were from Boehringer Mannheim or Santa Cruz. Anti-β-galactosidase antibody was from Chemicon. Protein G-agarose was purchased from Boehringer Mannheim. Peroxidase conjugated anti-mouse IgG was obtained from Amersham Life Science. Primary cultures of neonatal cardiac myocytes were prepared as described previously (Foncea R, et al., *J. Biol. Chem.*, 1997, 272:19115-19124). Cultures were enriched with cardiac myocytes by preplating for 60 minutes to eliminate fibroblasts. Over 90% of the cells were identified as cardiac myocytes by immunocytochemistry with anti-sarcomeric α-actin (Sigma). Attached cells were passaged once and used as the fibroblast fraction. Cell viability was determined using the trypan-blue exclusion assay. Surviving cell number is expressed relative to the initial cell number. Alternatively, cells were scored for condensed or pyknotic nuclei following fixation in 3.7% formaldehyde and staining with Hoechst 33342. In some assays, cells were pretreated with wortmannin for 30 minutes and incubated in the medium containing wortmannin in the presence or absence of IGF-1. Dimethyl sulfoxide was used as the vehicle for the wortmannin at concentration of 0.1% (vol/vol). Control cultures received the vehicle alone. Akt kinase assays were performed on anti-Akt or anti-HA immunoprecipitates from cell lysates as described previously using histone H2B (Songyang Z, et al., *Proc. Natl. Acad. Sci. USA*, 1997, 94:11345-11350). Immunoblots were performed as described previously (earlier Examples and Guo K, et al., *Mol. Cell. Biol*, 1995, 15:3823-3829).

DNA ladder and TUNEL analyses with cultured myocytes: DNA ladder experiments were performed as described in the foregoing examples.

Adenoviral constructs: Wild-type, dominant-negative and constitutively-active forms of human Akt were tagged with the HA epitope were constructed as described in the foregoing examples. The dominant-negative Akt mutant (Adeno-dnAkt) has alanine residues substituted for threonine at position 308 and serine at position 473. The constitutively-active Akt (Adeno-myrAkt) has the c-src myristoylation sequence fused in-frame to the N-terminus of the wild-type Akt coding sequence that targets the fusion protein to the membrane. Viral vectors expressing wild-type (wtAkt) or mutant Akt genes or lacZ (Adeno-βgal) from the CMV promoter were purified by CsCl ultracentrifugation. Myocytes were plated in M199 containing 10% FCS overnight and then incubated with adenovirus vector at the multiplicity of infection of 25 in M199 containing 2% FCS. After an overnight incubation, the virus was removed and cells were cultured in serum-free M199. Adenovirus transduction in vivo transgene detection TUNEL and Evans blue staining: Eleven C57BL/6J mice (6-8 weeks old) were anesthetized with methoxyflurane and ventilated with a rodent respirator attached to a nose cone. A mixture of Adeno-myrAkt ($6 \times 10^7$ pfu/mouse) plus Adeno-βgal ($1 \times 10^7$ pfu/mouse), or Adeno-βgal ($7 \times 10^7$ pfu/mouse) alone, in 15 μl of PBS with 10% glycerol was quickly injected into the apex and anterolateral wall of the heart using a 26 gauge needle (Agah R, et al., *J. Clin. Invest*, 1997, 100:2722-2728). Twenty hours later, animals were subjected to sham operation or left coronary artery occlusion for 45 minutes followed by 4 hours or reperfusion. Hearts were frozen immediately after sacrifice and sections (10 μm) were prepared with a Microm HM505E (Zeiss). Sections were fixed with 4% paraformaldehyde in PBS for 15 min and stained with Hoechst 33342 and anti-HA or anti-β-galactosidase antibody. The same sections were also stained with TUNEL to detect apoptotic cells according to the manufacturer's protocol (Boehringer). Secondary antibodies labeled with rhodamine (Pierce) were used for the detection of HA-Akt-positive or β-galactosidase-positive cells. Myocyte identity was indicated by staining with anti-α-sarcomeric actin antibody, using Cy5-labeled secondary antibody (Accurate Chemical and Scientific Corp.). Alternatively, section were stained with X-gal. For animals subjected to ischemia-reperfusion injury, sections corresponding to the left ventricular free wall were analyzed by first viewing the fluorescein channel to locate the region of injury as indicated by TUNEL-positive nuclei. TUNEL-positive microscopic fields were then assessed for cells staining positive for HA-Akt or β-galactosidase transgenes. Once transgene-positive high power fields (400×) were identified, all myocytes within the field (approximately 200) were scored for transgene expression and TUNEL staining. Between two and three randomly chosen transgene-positive, high power fields were examined for each mouse. The percentage of transgene-positive and -negative myocytes that were TUNEL-positive were compared in each group to assess whether adenovirus-mediated myrAkt gene delivery inhibited ischemic-reperfusion-induced myocyte apoptosis in vivo. For sham operated animals, sections of the left ventricular wall were first scored for HA-tagged Akt, then for TUNEL staining in sections corresponding to the left ventricular free wall. A separate group of mice were subjected to sham operation, coronary occlusion or coronary occlusion followed by reperfusion. Regions of myocardial perfusion under each condition were assessed by staining with Evans blue dye (Sigma) as described previously (Bialik S, et al., *J. Clin. Invest.*, 1997, 100:1363-1372).

Statistical analysis: All data were evaluated with two tail, unpaired Student's t test, and expressed as the mean ±S.E.M. A values of $p<0.05$ was considered significant.

Results

IGF-1 protects cardiac myocytes under conditions of serum deprivation: Serum deprivation induces apoptosis in cultured cardiomyocytes (Wang L, et al., *Circ. Res.*, 1998, 83:516-522; Sheng Z, et al., *J. Biol. Chem.*, 1997, 272:5783-5791). To document the cytoprotective effects of IGF-1 under the conditions of our assays, neonatal rat cardiac myocytes were cultured in serum-free media in the presence or absence of IGF-1, and cell viability was determined by trypan-blue exclusion at various time points. In the absence of IGF-1, cardiac myocyte cultures displayed a time-dependent decrease in viability with greater than a 50% loss of live cells by 72 hours. However, cardiac myocyte viability was maintained in the presence of IGF-1. In contrast to the myocyte fraction of cells, passaged non-myocyte cells (fibroblasts) prepared from neonatal heart were resistant to death induced by serum deprivation. The insensitivity of cardiac fibroblasts to serum deprivation-induced cell death has been reported previously (Sheng Z, et al., *J. Biol. Chem.*, 1997, 272:5783-5791). Cardiomyocyte protection was dependent on the dose of IGF-1. IGF-1-induced cytoprotection was abrogated by treatment with 200 nM wortmannin, suggesting that the survival effects of IGF-1 is regulated by effector proteins downstream of PI 3-kinase. In the absence of IGF-1, wortmannin had no effect on cardiomyocyte viability. To provide additional evidence that these treatments influence cell death, cultures were fixed and stained with Hoechst 33342 to assay for chromosomal condensation, one indicator of apoptosis. IGF-1 suppressed the incidence of pyknotic nuclei, and this effect was reversed by the inclusion of wortmannin in the culture media.

Adenoviral transfection of wild-type, dominant-negative, or constitutively-active Akt in cultured cardiomyocytes: To determine the functional significance of Akt activation in IGF-1-stimulated cardiac myocyte cultures, replication-defective adenoviral vectors expressing wild-type and mutant forms of Akt fused to the hemagglutinin (HA) epitope were constructed. The mutant Akt [T308A, S473A] cannot be activated by phosphorylation (Alessi D R, et al., *EMBO J*, 1996, 15:6541-6551), and it functions in a dominant-negative manner. Cardiac myocytes were infected overnight with adenovirus vectors at multiplicity of infection of 25, and expression of exogenous Akt proteins was demonstrated by Western immunoblot analysis with anti-HA antibody. To analyze the kinase activities of adenovirally-encoded Akt proteins, parallel serum-deprived cultures were incubated in the presence or absence of IGF-1. Specific Akt protein kinase activity was detected in extracts from cells infected with the wild-type Akt vector in the presence, but not absence, of IGF-1 stimulation. The vector expressing dominant-negative Akt was inactive with regard to kinase activity. In contrast, cells infected with the vector expressing constitutively-active Akt displayed high levels of kinase activity in the presence or absence of IGF-1.

Cardiac myocyte cultures were infected with an adenoviral vector expressing dominant-negative Akt mutant to test whether Akt is essential for IGF-1-mediated survival. Infection with the dominant-negative Akt vector largely eliminated the increase in cell survival resulting from the inclusion of 25 or 50 ng/ml IGF-1 in the culture medium. In the absence of IGF-1, Adeno-dnAkt did not affect cardiomyocyte survival, indicating the specificity of dnAkt action. The control adenoviral construct expressing β-galactosidase (Adeno-βgal) had no detectable effect on myocyte viability. Furthermore, infection with Adeno-βgal did not affect Akt activity in cardiomyocytes.

To investigate the consequences of Akt overexpression on myocyte survival, cells were transfected with adenoviral vectors expressing wild-type Akt or β-galactosidase and cultured without serum in the absence or presence of IGF-1. Overexpression of wild-type Akt had no significant effect on survival in the absence of IGF-1, but cell survival was promoted by Akt overexpression in the presence of a sub-saturating concentration of IGF-1. At higher IGF-1 concentrations, overexpression of Akt had little or no effect on cell viability. These data show that Akt gene transfer enhances the survival effects of IGF-1, indicating that Akt is a critical factor in survival of cardiac myocytes under these conditions.

The effects of constitutively-active Akt on cardiomyocyte cultures was also assessed. Infection with Adeno-myrAkt produced cell shape changes similar to that reported in stably-transfected PAE cells (Welch H, et al., *J. Biol. Chem.*, 1998, 273:11248-11256). These cell shape changes obscured assessments of viability with the trypan-blue exclusion assay or staining with Hoechst 33342 to detect nuclear condensation. Thus, DNA fragmentation was assessed in cultures infected with Adeno-myrAkt or the control vector Adeno-βgal. DNA prepared from serum-deprived cardiomyocyte cultures infected with Adeno-βgal displayed the nucleosome spacing ladder following gel electrophoresis that is indicative of apoptosis. This DNA ladder was diminished, but not eliminated, in serum-deprived cultures infected with Adeno-myrAkt, suggesting that this agent inhibits apoptotic cell death in the absence of exogenous IGF-1 stimulation.

TUNEL analyses were performed to examine the effects of the different Akt-expressing adenovirus vectors on cardiomyocyte survival in vitro. Cells were infected with the indicated adenovirus vector or mock-infected overnight, and then cultured in the serum-depleted media in the presence of the indicated concentrations of IGF-1 for 48 hours. Apoptotic cells were identified by TUNEL and Hoechst staining, and staining with anti-α-sarcomeric actin was performed to confirm myocyte identity. Increasing concentrations of IGF-1 reduced the frequency of myocyte apoptosis in mock- and Adeno-β-gal-transfected cells. Infection with adenovirus expressing dominant-negative Akt blocked the protective effects of IGF-1. Infection with adenovirus expressing wild-type Akt facilitated IGF-1-mediated cardiomyocyte survival at low IGF-1 concentrations, whereas infection with adenovirus expressing constitutively-active Akt reduced the frequency of myocyte apoptosis in the absence of IGF-1 or at low concentrations of IGF-1. Of note, Adeno-myrAkt did not have an additive effect on survival at saturating IGF-1 (50 ng/ml), suggesting further that Akt activation is an integral feature of the IGF-1 survival pathway in cardiomyocytes.

Figure 6:
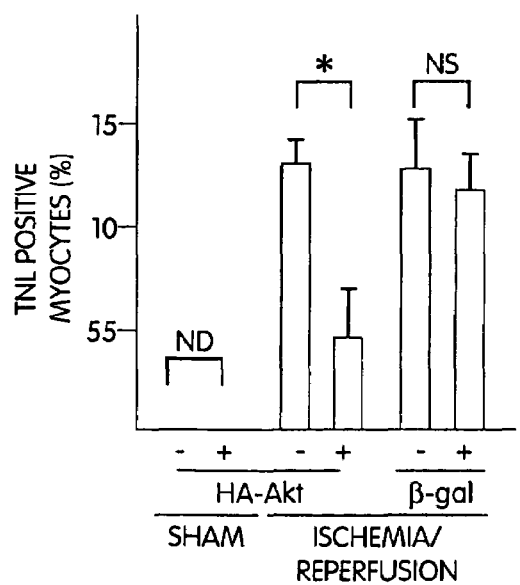
FIG. 6. Quantitative analysis of the in vivo cardioprotective effects of myrAkt.

Constitutively-active Akt protects myocardium from apoptosis following reperfusion injury: Reperfusion of ischemic myocardium is reported to accelerate myocyte apoptosis (Fliss H, and Gattinger D., Circ. Res., 1996, 79:949-956), and IGF-1 can protect myocardium under these conditions (Buerke M, et al., Proc. Natl. Acad. Sci. USA, 1995, 92:8031-8035). Thus, we investigated whether expression of constitutively-active Akt could protect murine myocardium from reperfusion injury. In this model, adenoviral constructs were directly injected into the apical and anterolateral free wall of the heart, a region that shows a large perfusion defect following occlusion of the left coronary artery as determined by staining with Evans blue dye. Evans blue staining was uniform following removal of the ligature, consistent with restored perfusion. Direct adenovirus injection resulted in transgene expression localized to cells adjacent to the track of the needle and confined to myocardium subject to hypoperfusion. To examine the effects of constitutive Akt expression on myocyte viability in vivo, mouse hearts were injected with Adeno-myrAkt or the Adeno-βgal control vector 20 hours prior to ischemia-reperfusion injury or sham operation. Sections of heart were analyzed for transgene expression by immunohistochemical detection of the HA epitope (myrAkt) or β-galactosidase, and cell death was assessed by TUNEL staining. Cells with apoptotic nuclei were identified as cardiac myocytes by staining with anti-α-sarcomeric actin antibody. High power microscopic fields (approximately 200 Hoechst-positive myocytes/per field) were identified that contained transgene-positive cells. Systematic analyses of these fields revealed that myocardial cells expressing HA-tagged myrAkt displayed significantly fewer TUNEL-positive nuclei than immediately adjacent cells that were negative for transgene expression (FIG. 6). In contrast to cultured myocytes, no obvious morphological alterations were apparent in the cells expressing myrAkt. Mouse hearts injected with Adeno-βgal and subjected to ischemia-reperfusion injury displayed no differences in TUNEL-positive staining between cells that were positive or negative for β-galactosidase transgene expression. TUNEL-positive cells were not identified in either HA-myrAkt-positive or -negative cells of sham operated animals.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is presented below and is followed by a Sequence Listing.

I claim:

1. A method for treating myocardial infarction, comprising:
administering to a subject in need of such treatment a composition comprising a replication-defective adenovirus comprising a polynucleotide, wherein said composition is administered acutely into apical and anterolateral free wall of heart, wherein said polynucleotide comprises a nucleotide sequence that encodes an Akt polypeptide, operatively linked to a promoter to promote expression of the Akt polypeptide in cardiomyocytes, wherein the Akt polypeptide comprises the amino acid sequence of SEQ ID NO:2.

2. The method of claim 1, wherein the polynucleotide consists of a nucleotide sequence that encodes the Akt polypeptide comprising the amino acid sequence of SEQ ID NO:2.

3. The method of claim 1, wherein the polynucleotide has a nucleotide sequence comprising SEQ ID NO:1.

4. The method of claim 1, wherein the polynucleotide has a nucleotide sequence consisting of SEQ ID NO:1.

* * * * *

SEQUENCE LISTING

```
<160> NUMBER OF SEQ ID NOS: 8

<210> SEQ ID NO 1
<211> LENGTH: 2610
<212> TYPE: DNA
<213> ORGANISM: Homo Sapiens

<400> SEQUENCE: 1
atcctgggac agggcacagg gccatctgtc accaggggct tagggaaggc cgagccagcc      60
tgggtcaaag aagtcaaagg ggctgcctgg aggaggcagc ctgtcagctg gtgcatcaga     120
ggctgtggcc aggccagctg ggctcgggga gcgccagcct gagaggagcg cgtgagcgtc     180
gcgggagcct cgggcaccat gagcgacgtg gctattgtga aggagggttg gctgcacaaa     240
cgaggggagt acatcaagac ctggcggcca cgctacttcc tcctcaagaa tgatggcacc     300
ttcattggct acaaggagcg gccgcaggat gtggaccaac gtgaggctcc cctcaacaac     360
ttctctgtgg cgcagtgcca gctgatgaag acggagcggc cccggcccaa caccttcatc     420
atccgctgcc tgcagtggac cactgtcatc gaacgcacct tccatgtgga gactcctgag     480
gagcgggagg agtggacaac cgccatccag actgtggctg acgcctcaa gaagcaggag     540 gaggaggaga tggacttccg gtcgggctca cccagtgaca actcagggc tgaagagatg     600 gaggtgtccc tggccaagcc caagcaccgc gtgaccatga acgagtttga gtacctgaag     660
ctgctgggca agggcacttt cggcaaggtg atcctggtga aggagaaggc cacaggccgc     720
tactacgcca tgaagatcct caagaaggaa gtcatcgtgg ccaaggacga ggtggccac      780 acactcaccg agaaccgcgt cctgcagaac tccaggcacc ccttcctcac agccctgaag     840
```

-continued

```
tactctttcc agacccacga ccgcctctgc tttgtcatgg agtacgccaa cgggggcgag    900
ctgttcttcc acctgtcccg ggaacgtgtg ttctccgagg accgggcccg cttctatggc    960
gctgagattg tgtcagccct ggactacctg cactcggaga agaacgtggt gtaccgggac   1020
ctcaagctgg agaacctcat gctggacaag gacgggcaca ttaagatcac agacttcggg   1080
ctgtgcaagg aggggatcaa ggacggtgcc accatgaaga ccttttgcgg cacacctgag   1140
tacctggccc ccgaggtgct ggaggacaat gactacggcc gtgcagtgga ctggtggggg   1200
ctgggcgtgg tcatgtacga gatgatgtgc ggtcgcctgc ccttctacaa ccaggaccat   1260
gagaagcttt ttgagctcat cctcatggag agatccgct tcccgcgcac gcttggtccc    1320
gaggccaagt ccttgctttc agggctgctc aagaaggacc ccaagcagag gcttggcggg   1380
ggctccgagg acgccaagga gatcatgcag catcgcttct tgccggtat cgtgtggcag    1440
cacgtgtacg agaagaagct cagcccaccc ttcaagcccc aggtcacgtc ggagactgac   1500
accaggtatt ttgatgagga gttcacggcc cagatgatca ccatcacacc acctgaccaa   1560
gatgacagca tggagtgtgt ggacagcgag cgcaggcccc acttccccca gttctcctac   1620
tcggccagca gcacggcctg aggcggcggt ggactgcgct ggacgatagc ttggagggat   1680
ggagaggcgg cctcgtgcca tgatctgtat ttaatggttt ttatttctcg ggtgcatttg   1740
agagaagcca cgctgtcctc tcgagcccag atggaaagac gttttttgtgc tgtgggcagc   1800
accctccccc gcagcggggt agggaagaaa actatcctgc gggtttttaat ttatttcatc   1860
cagtttgttc tccgggtgtg gcctcagccc tcagaacaat ccgattcacg tagggaaatg   1920
ttaaggactt ctacagctat cgcaatgtg gcattggggg gccgggcagg tcctgcccat    1980
gtgtcccctc actctgtcag ccagccgccc tgggctgtct gtcaccagct atctgtcatc   2040
tctctggggc cctgggcctc agttcaacct ggtggcacca gatgcaacct cactatggta   2100
tgctggccag caccctctcc tggggtgtgc aggcacacag cagccccca gcactaaggc    2160
cgtgtctctg aggacgtcat cggaggctgg gcccctggga tgggaccagg gatgggggat   2220
gggccagggt ttacccagtg ggacagagga gcaaggttta aatttgttat tgtgtattat   2280
gttgttcaaa tgcattttgg gggtttttaa tctttgtgac aggaaagccc tccccctttcc   2340
ccttctgtgt cacagttctt ggtgactgtc ccaccggagc ctccccctca gatgatctct   2400
ccacggtagc acttgacctt ttcgacgctt aacctttccg ctgtcgcccc aggccctccc   2460
tgactccctg tgggggtggc catccctggg cccctccacg cctcctggcc agacgctgcc   2520
gctgccgctg caccacggcg ttttttttaca acattcaact ttagtatttt tactattata   2580
atataatatg gaaccttccc tccaaattct                                    2610
```

<210> SEQ ID NO 2
<211> LENGTH: 480
<212> TYPE: PRT
<213> ORGANISM: Homo Sapiens
<220> FEATURE:
<221> NAME/KEY: DOMAIN
<222> LOCATION: (5)...(108)
<223> OTHER INFORMATION: Pleckstrin Homology
<220> FEATURE:
<221> NAME/KEY: DOMAIN
<222> LOCATION: (150)...(408)
<223> OTHER INFORMATION: Serine-Threonine Kinase

<400> SEQUENCE: 2

```
Met Ser Asp Val Ala Ile Val Lys Glu Gly Trp Leu His Lys Arg Gly
 1               5                  10                  15
```

```
Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
             35                  40                  45

Glu Ala Pro Leu Asn Asn Phe Ser Val Ala Gln Cys Gln Leu Met Lys
 50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
             85                  90                  95

Glu Glu Trp Thr Thr Ala Ile Gln Thr Val Ala Asp Gly Leu Lys Lys
             100                 105                 110

Gln Glu Glu Glu Glu Met Asp Phe Arg Ser Gly Ser Pro Ser Asp Asn
             115                 120                 125

Ser Gly Ala Glu Glu Met Glu Val Ser Leu Ala Lys Pro Lys His Arg
 130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
             165                 170                 175

Ala Met Lys Ile Leu Lys Lys Glu Val Ile Val Ala Lys Asp Glu Val
             180                 185                 190

Ala His Thr Leu Thr Glu Asn Arg Val Leu Gln Asn Ser Arg His Pro
             195                 200                 205

Phe Leu Thr Ala Leu Lys Tyr Ser Phe Gln Thr His Asp Arg Leu Cys
 210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
             245                 250                 255

Ile Val Ser Ala Leu Asp Tyr Leu His Ser Glu Lys Asn Val Val Tyr
             260                 265                 270

Arg Asp Leu Lys Leu Glu Asn Leu Met Leu Asp Lys Asp Gly His Ile
             275                 280                 285

Lys Ile Thr Asp Phe Gly Leu Cys Lys Glu Gly Ile Lys Asp Gly Ala
 290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
             325                 330                 335

Val Val Met Tyr Glu Met Met Cys Gly Arg Leu Pro Phe Tyr Asn Gln
             340                 345                 350

Asp His Glu Lys Leu Phe Glu Leu Ile Leu Met Glu Glu Ile Arg Phe
             355                 360                 365

Pro Arg Thr Leu Gly Pro Glu Ala Lys Ser Leu Leu Ser Gly Leu Leu
             370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
             405                 410                 415

Tyr Glu Lys Lys Leu Ser Pro Pro Phe Lys Pro Gln Val Thr Ser Glu
             420                 425                 430

Thr Asp Thr Arg Tyr Phe Asp Glu Glu Phe Thr Ala Gln Met Ile Thr
```

|     | 435 |     |     |     | 440 |     |     |     |     | 445 |     |     |
| --- | --- | --- | --- | --- | --- | --- | --- | --- | --- | --- | --- | --- |

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 3
<211> LENGTH: 1254
<212> TYPE: DNA
<213> ORGANISM: Homo Sapiens

<400> SEQUENCE: 3

| | | | | |
|---|---|---|---|---|
| atgaagacgg | agcggccccg | gcccaacacc | ttcatcatcc | gctgcctgca gtggaccact | 60 |
| gtcatcgaac | gcaccttcca | tgtggagact | cctgaggagc | gggaggagtg gacaaccgcc | 120 |
| atccagactg | tggccgacgg | cctcaagaag | caggaggagg | aggagatgga cttccggtcg | 180 |
| ggctcaccca | gcgacaactc | aggggccgaa | gagatggagg | tgtccctggc caagcccaag | 240 |
| caccgcgtga | ccatgaacga | gtttgagtac | ctgaagctgc | tgggcaaggg cactttcggc | 300 |
| aaggtgatcc | tggtgaagga | gaaggccaca | gcgtactacg | ccatgaagat cctcaagaag | 360 |
| gaagtcatcg | tggccaagga | cgaggtggcc | cacacactca | ccgagaaccg cgtccagcag | 420 |
| aactccaggc | accccttcct | cactcgcctg | aagtactctt | tccagaccca cgaccgcctc | 480 |
| tgctttgtca | tggagtacgc | caacgggggc | gagctgttct | tccacctgtc ccgggagcgt | 540 |
| gtgttcgccg | aggaccgggc | ccgcttctat | ggcgctgaga | ttgtgtcagc cctggactac | 600 |
| ctgcactcgg | agaagaacgt | ggtgtaccgg | gacctcaagc | tggagaacct catgctggac | 660 |
| aaggacgggc | acattaagat | cacagacttc | gggctgtgca | aggaggggat caaggacggt | 720 |
| gccaccatga | agacctttg | cggcacacct | gagtacctgg | cccccgaggt gctggaggac | 780 |
| aatgactacg | gccgtgcagt | ggactggtgg | gggctgggcg | tggtcatgta cgagatgatg | 840 |
| tgcggtcgcc | tgcccttcta | caaccaggac | catgagaagc | tttttgagct catcctcatg | 900 |
| gaggagatcc | gcttcccgcg | cacgcttggt | cccgaggcca | gtccttgct ttcagggctg | 960 |
| ctcaagaagg | accccaagca | gaggcttggc | gggggctccg | aggacgccaa ggagatcatg | 1020 |
| cagcatcgct | tctttaccgg | tatcgtgtgg | cagcacgtgt | acgagaagaa gctcagccca | 1080 |
| cccttcaagc | cccaggtcac | gtcggagact | gacaccaggt | attttgatga ggagttcacg | 1140 |
| gcccagatga | tcaccatcac | accacctgac | caagatgaca | gcatggagtg tgtggacagc | 1200 |
| gagcgcaggc | cccacttccc | ccagttctcc | tactcgccca | gcgcgacggc ctga | 1254 |

<210> SEQ ID NO 4
<211> LENGTH: 417
<212> TYPE: PRT
<213> ORGANISM: Homo Sapiens

<400> SEQUENCE: 4

Met Lys Thr Glu Arg Pro Arg Pro Asn Thr Phe Ile Ile Arg Cys Leu
1               5                   10                  15

Gln Trp Thr Thr Val Ile Glu Arg Thr Phe His Val Glu Thr Pro Glu
                20                  25                  30

Glu Arg Glu Glu Trp Thr Thr Ala Ile Gln Thr Val Ala Asp Gly Leu
            35                  40                  45

Lys Lys Gln Glu Glu Glu Glu Met Asp Phe Arg Ser Gly Ser Pro Ser
        50                  55                  60

Asp Asn Ser Gly Ala Glu Glu Met Glu Val Ser Leu Ala Lys Pro Lys

-continued

```
                65                  70                  75                  80
His Arg Val Thr Met Asn Glu Phe Glu Tyr Leu Lys Leu Leu Gly Lys
                    85                  90                  95
Gly Thr Phe Gly Lys Val Ile Leu Val Lys Glu Lys Ala Thr Ala Tyr
                100                 105                 110
Tyr Ala Met Lys Ile Leu Lys Lys Glu Val Ile Val Ala Lys Asp Glu
                115                 120                 125
Val Ala His Thr Leu Thr Glu Asn Arg Val Gln Gln Asn Ser Arg His
            130                 135                 140
Pro Phe Leu Thr Arg Leu Lys Tyr Ser Phe Gln Thr His Asp Arg Leu
145                 150                 155                 160
Cys Phe Val Met Glu Tyr Ala Asn Gly Gly Glu Leu Phe Phe His Leu
                165                 170                 175
Ser Arg Glu Arg Val Phe Ala Glu Asp Arg Ala Arg Phe Tyr Gly Ala
                180                 185                 190
Glu Ile Val Ser Ala Leu Asp Tyr Leu His Ser Glu Lys Asn Val Val
                195                 200                 205
Tyr Arg Asp Leu Lys Leu Glu Asn Leu Met Leu Asp Lys Asp Gly His
            210                 215                 220
Ile Lys Ile Thr Asp Phe Gly Leu Cys Lys Glu Gly Ile Lys Asp Gly
225                 230                 235                 240
Ala Thr Met Lys Thr Phe Cys Gly Thr Pro Glu Tyr Leu Ala Pro Glu
                245                 250                 255
Val Leu Glu Asp Asn Asp Tyr Gly Arg Ala Val Asp Trp Trp Gly Leu
                260                 265                 270
Gly Val Val Met Tyr Glu Met Met Cys Gly Arg Leu Pro Phe Tyr Asn
                275                 280                 285
Gln Asp His Glu Lys Leu Phe Glu Leu Ile Leu Met Glu Glu Ile Arg
            290                 295                 300
Phe Pro Arg Thr Leu Gly Pro Glu Ala Lys Ser Leu Leu Ser Gly Leu
305                 310                 315                 320
Leu Lys Lys Asp Pro Lys Gln Arg Leu Gly Gly Gly Ser Glu Asp Ala
                325                 330                 335
Lys Glu Ile Met Gln His Arg Phe Phe Thr Gly Ile Val Trp Gln His
                340                 345                 350
Val Tyr Glu Lys Lys Leu Ser Pro Pro Phe Lys Pro Gln Val Thr Ser
                355                 360                 365
Glu Thr Asp Thr Arg Tyr Phe Asp Glu Glu Phe Thr Ala Gln Met Ile
            370                 375                 380
Thr Ile Thr Pro Pro Asp Gln Asp Asp Ser Met Glu Cys Val Asp Ser
385                 390                 395                 400
Glu Arg Arg Pro His Phe Pro Gln Phe Ser Tyr Ser Pro Ser Ala Thr
                405                 410                 415
Ala
```

<210> SEQ ID NO 5
<211> LENGTH: 2626
<212> TYPE: DNA
<213> ORGANISM: Mus Musculus

<400> SEQUENCE: 5

```
ccgggaccag cggacggacc gagcagcgtc ctgcggccgg caccgcggcg gcccagatcc    60
ggccagcagc gcgcgcccgg acgccgctgc cttcagccgg ccccgcccag cgcccgcccg   120
```

-continued

| | |
|---|---|
| cgggatgcgg agcggcgggc gcccgaggcc gcggcccgc taggcccagt cgcccgcacg | 180 |
| cggcggcccg acgctgcggc caggccggct gggctcagcc taccgagaag agactctgat | 240 |
| catcatccct gggttacccc tgtctctggg ggccacggat accatgaacg acgtagccat | 300 |
| tgtgaaggag ggctggctgc acaaacgagg ggaatatatt aaaacctggc ggccacgcta | 360 |
| cttcctcctc aagaacgatg gcacctttat tggctacaag gaacggcctc aggatgtgga | 420 |
| tcagcgagag tccccactca caacttctc agtggcacaa tgccagctga tgaagacaga | 480 |
| gcggccaagg cccaacacct ttatcatccg ctgcctgcag tggaccacag tcattgagcg | 540 |
| caccttccat gtgaaacgc ctgaggagcg ggaagaatgg gccaccgcca ttcagactgt | 600 |
| ggccgatgga ctcaagaggc aggaagaaga gacgatggac ttccgatcag gctcacccag | 660 |
| tgacaactca ggggctgaag agatggaggt gtccctggcc aagcccaagc accgtgtgac | 720 |
| catgaacgag tttgagtacc tgaaactact gggcaagggc acctttggga aagtgattct | 780 |
| ggtgaaagag aaggccacag gccgctacta tgccatgaag atcctcaaga aggaggtcat | 840 |
| cgtcgccaag gatgaggttg cccacacgct tactgagaac cgtgtcctgc agaactctag | 900 |
| gcatcccttc cttacggccc tcaagtactc attccagacc cacgaccgcc tctgctttgt | 960 |
| catggagtat gccaacgggg gcgagctctt cttccacctg tctcgagagc gcgtgttctc | 1020 |
| cgaggaccgg gcccgcttct atggtgcgga gattgtgtct gccctggact acttgcactc | 1080 |
| cgagaagaac gtggtgtacc gggacctgaa gctggagaac ctcatgctgg acaaggacgg | 1140 |
| gcacatcaag ataacggact cgggctgtg caaggagggg atcaaggatg gtgccactat | 1200 |
| gaagacattc tgcggaacgc cggagtacct ggcccctgag gtgctggagg acaacgacta | 1260 |
| cggccgtgca gtggactggt gggggctggg cgtggtcatg tatgagatga tgtgtggccg | 1320 |
| cctgcccttc tacaaccagg accacgagaa gctgttcgag ctgatcctca tggaggagat | 1380 |
| ccgcttcccg cgcacactcg gccctgagcc caagtccctg ctctccgggc tgctcaagaa | 1440 |
| ggaccctaca cagaggctcg gtgggggctc tgaggatgcc aaggagatca tgcagcaccg | 1500 |
| gttctttgcc aacatcgtgt ggcaggatgt gtatgagaag aagctgagcc cacctttcaa | 1560 |
| gccccaggtc acctctgaga ctgacaccag gtatttcgat gaggagttca cagctcagat | 1620 |
| gatcaccatc acgccgcctg atcaagatga cagcatggag tgtgtggaca gtgagcggag | 1680 |
| gccgcacttc ccccagttct cctactcagc cagtggcaca gcctgaggcc tggggcagcg | 1740 |
| gctggcagct ccacgctcct ctgcattgcc gagtccagaa gccccgcatg gatcatctga | 1800 |
| acctgatgtt ttgttctcg gatgcgctgg ggaggaacct tgccagcctc caggaccagg | 1860 |
| ggaggatgtt tctactgtgg gcagcagcct acctcccagc caggtcagga ggaaaactat | 1920 |
| cctggggttt ttcttaattt atttcatcca gtttgagacc acacatgtgg cctcagtgcc | 1980 |
| cagaacaatt agattcatgt agaaaactat taaggactga cgcgaccatg tgcaatgtgg | 2040 |
| gctcatgggt ctgggtgggt cccgtcactg ccccattgg cctgtccacc ctggccgcca | 2100 |
| cctgtctcta gggtccaggg ccaaagtcca gcaagaaggc accagaagca cctccctgtg | 2160 |
| gtatgctaac tggcccctctc cctctgggcg gggagaggtc acagctgctt cagccctagg | 2220 |
| gctggatggg atggccaggg ctcaagtgag gttgacagag gaacaagaat ccagtttgtt | 2280 |
| gctgtgtccc atgctgttca gagacattta ggggatttta atcttggtga caggagagcc | 2340 |
| cctgccctcc cgctcctgcg tggtggctct tagcgggtac cctgggagcg cctgcctcac | 2400 |
| gtgagccctc tcctagcact tgtccttta gatgctttcc ctctcccgct gtccgtcacc | 2460 |
| ctggcctgtc ccctcccgcc agacgctggc cattgctgca ccatgtcgtt ttttacaaca | 2520 |

-continued

```
ttcagcttca gcatttttac tattataata agaaactgtc cctccaaatt caataaaaat    2580
tgcttttcaa gcttgaaaaa aaaaaaaaaa aaaaaaaaaa aaaaaa                   2626
```

<210> SEQ ID NO 6
<211> LENGTH: 480
<212> TYPE: PRT
<213> ORGANISM: Mus Musculus

<400> SEQUENCE: 6

```
Met Asn Asp Val Ala Ile Val Lys Glu Gly Trp Leu His Lys Arg Gly
  1               5                  10                  15

Glu Tyr Ile Lys Thr Trp Arg Pro Arg Tyr Phe Leu Leu Lys Asn Asp
                 20                  25                  30

Gly Thr Phe Ile Gly Tyr Lys Glu Arg Pro Gln Asp Val Asp Gln Arg
             35                  40                  45

Glu Ser Pro Leu Asn Asn Phe Ser Val Ala Gln Cys Gln Leu Met Lys
         50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Ala Thr Ala Ile Gln Thr Val Ala Asp Gly Leu Lys Arg
                100                 105                 110

Gln Glu Glu Glu Thr Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350
```

```
Asp His Glu Lys Leu Phe Glu Leu Ile Leu Met Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Thr Gln Arg Leu Gly Gly Gly Ser Glu Asp Ala Lys
385                 390                 395                 400

Glu Ile Met Gln His Arg Phe Phe Ala Asn Ile Val Trp Gln Asp Val
                405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Gly Thr Ala
465                 470                 475                 480

<210> SEQ ID NO 7
<211> LENGTH: 20
<212> TYPE: DNA
<213> ORGANISM: Homo Sapiens

<400> SEQUENCE: 7
tgtcaggctg gtctgcctcc                                              20

<210> SEQ ID NO 8
<211> LENGTH: 18
<212> TYPE: DNA
<213> ORGANISM: Homo Sapiens

<400> SEQUENCE: 8
tggatccgac atgtcaga                                                18
```